(12) United States Patent
Summerton

(10) Patent No.: US 7,132,393 B2
(45) Date of Patent: Nov. 7, 2006

(54) TRANSPORTER COMPOSITIONS AND METHODS FOR DETECTING AND KILLING CELLS IN ACIDIC AREAS OF TUMORS

(75) Inventor: James Edward Summerton, Corvallis, OR (US)

(73) Assignee: Gene Tools. LLC, Philomath, OR (US)

( * ) Notice: Subject to any disclaimer, the term of this patent is extended or adjusted under 35 U.S.C. 154(b) by 0 days.

(21) Appl. No.: 11/069,387

(22) Filed: Feb. 28, 2005

(65) Prior Publication Data

US 2006/0193774 A1 Aug. 31, 2006

(51) Int. Cl.
*A01N 37/18* (2006.01)
(52) U.S. Cl. .......................................... 514/2
(58) Field of Classification Search ............. None
See application file for complete search history.

(56) References Cited

U.S. PATENT DOCUMENTS 6,030,941 A * 2/2000 Summerton et al. ............ 514/2

OTHER PUBLICATIONS

Jahde, Volk, Atema, Smets, Glusenkamp, Rajewsky (1992) Cancer Research 52, 6209-6215).
Bernard, Krenning, Breeman, Rolleman, Bakker, Visser, Macke, de Jong, Journal of Nuclear Medicine 38, 1929 (1997).
Garcia-Garayoa, Blauenstein, Bruehlmrier, Blanc, Iterbeke, Conrath, Tourwe & Schubiger (2002), The Journal of Nuclear Medicine 43, 374-383.
Prescott, Charles, Poulson, Page, Thrall, Vujaskovic, & Dewhirst (2000) Clinical Cancer Research 6, 2501-2505.
Kozin, Shkarin, & Gerweck (2001) Cancer Research 61, 4740-4743.
Kuin, Smets, Volk, Paans, Adams, Atema, Jahde, Maas, Rajewsky, & Visser (1994) Cancer Research 54, 3785-3792.

* cited by examiner

Primary Examiner—Bruce R. Campell
Assistant Examiner—Satyanarayana R. Gudibande
(74) Attorney, Agent, or Firm—Lori M. Friedman

(57) ABSTRACT

Improved transporter compositions effective for detecting or killing cells in acidic areas of tumors are described. Each composition includes a transporter peptide which at pH 7.2 and above is poly-anionic and so repels from cells in normal tissues, but at lower pH in hypoxic areas of tumors the transporter peptide converts to a non-ionic lipophilic form which transports across membranes of cells. Each composition also includes a cargo component which can be pulled across cell membranes by the transporter peptide and which is effective for detecting or killing cells into which the transporter composition has entered.

25 Claims, 26 Drawing Sheets

Transporter mode of action

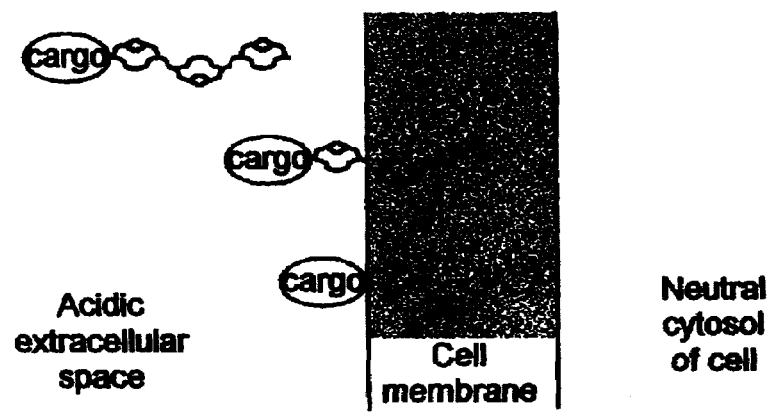
Comparative Figure 1a [RELATED ART].
Embedder mode of action

Expected area of activity of improved transporter compositions of invention

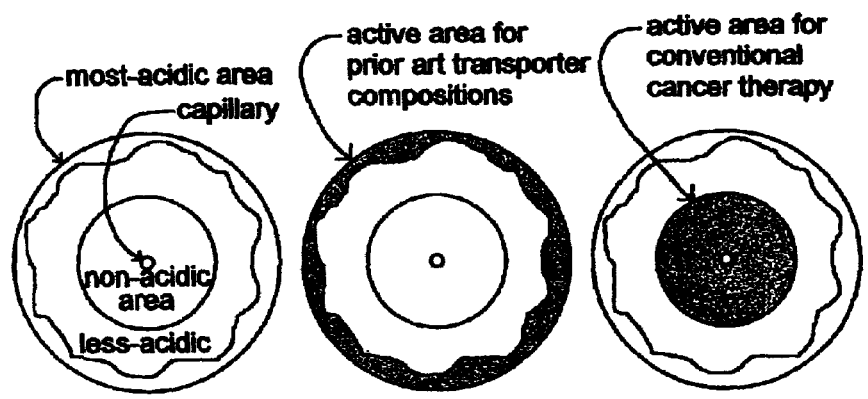
Comparative Figure 2a [PRIOR ART].
Expected area of activity of prior art transporter compositions Transporter composition: repelling from normal cell entering tumor cell

Figure 4.
Double-hydrogen-bonded acid pair structure
a) Transition between anionic and lipophilic
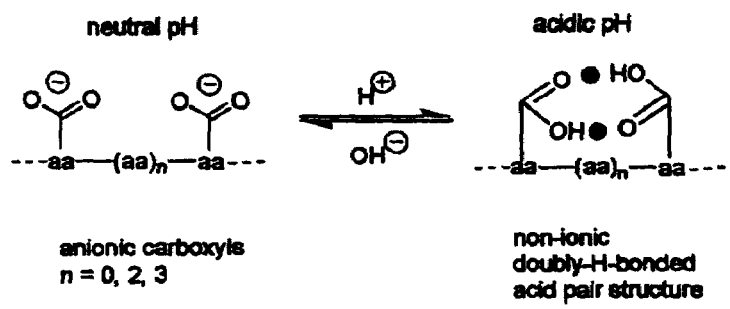
anionic carboxyls
n = 0, 2, 3
non-ionic
doubly-H-bonded
acid pair structure
b) Acid pair structure with 2 intervening amino acids
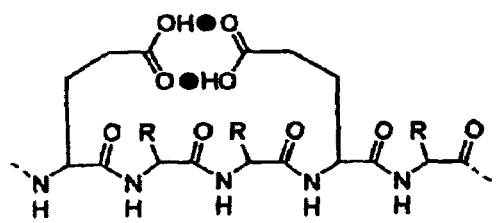

Figure 5a.
Axial distribution plots of acid pairs:
Sequences with poor axial distribution and
poor transporter activity
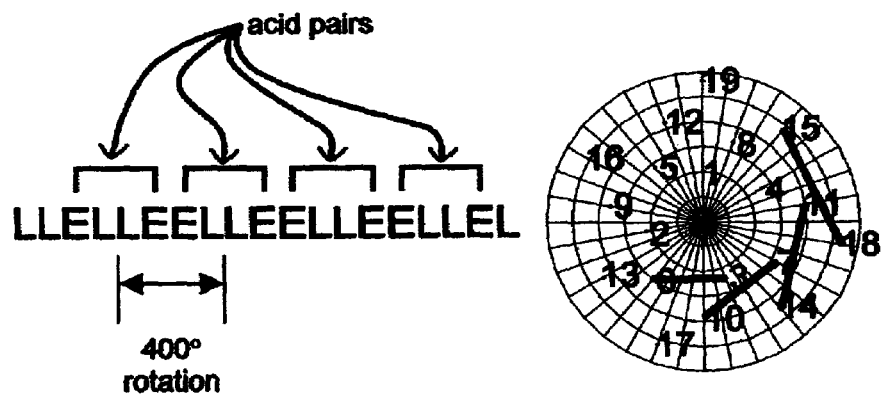
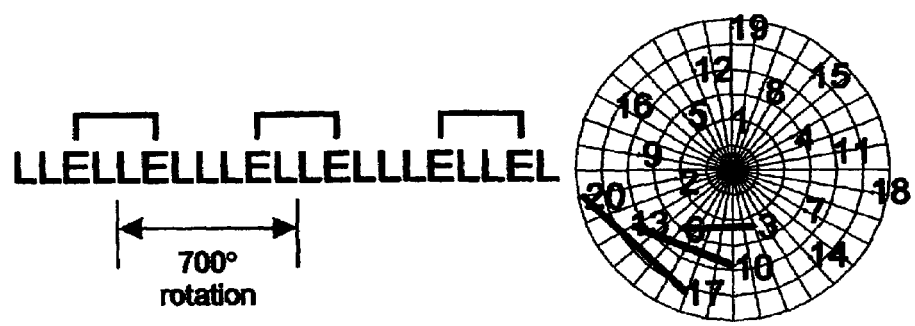

Figure 5b.
Axial distribution plots of acid pairs:
Sequences with good axial distribution and
good transporter activity
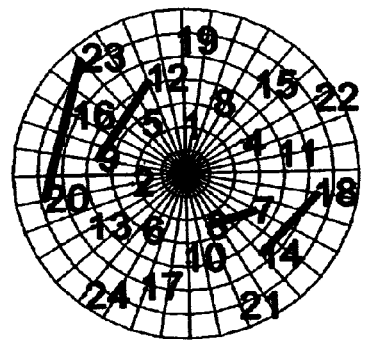
LLELLLELELELLELELLLELELLEA
550° rotation
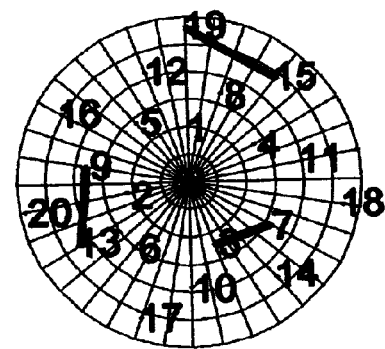
LLELLLELELELLLELELLLEL
600° rotation

Figure 6.

Key structural features for selecting transporter peptide sequences a) acid pair types

```
  ⊓
  EE         acid pair with no intervening amino acids
  |
centerpoint
of acid pair
```

```
  ⌐ ⌐
  ELLE       acid pair with two intervening amino acids
  |          (L is a lipophilic amino acid)
centerpoint
of acid pair
```

```
  ⌐  ⌐
  ELLLE      acid pair with three intervening amino acids
  |          (L is a lipophilic amino acid)
centerpoint
of acid pair
``` b) axial rotation values between adjacent acid pairs

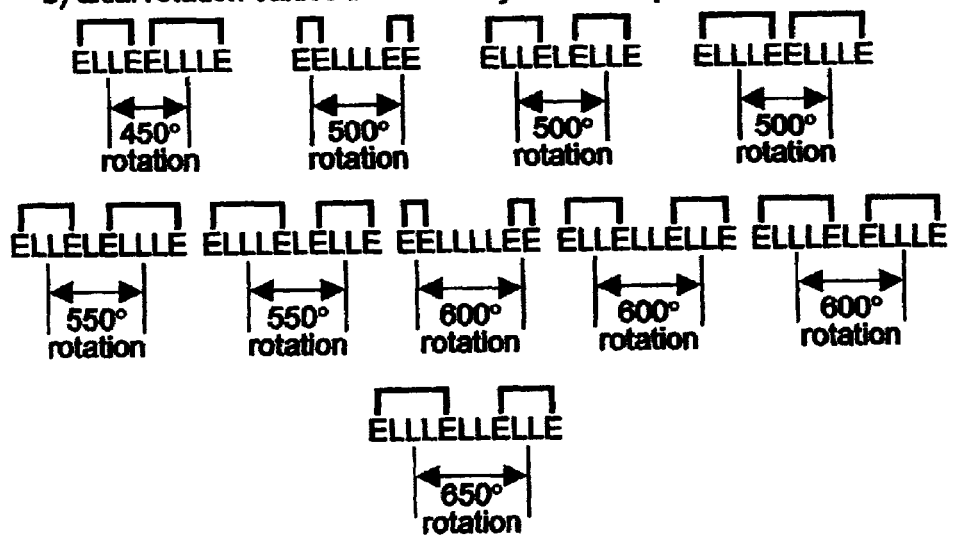

Figure 7.
Graphical selection of transporter peptide sequences
a) 550° rotation values, ELLE and ELLLE acid pair types
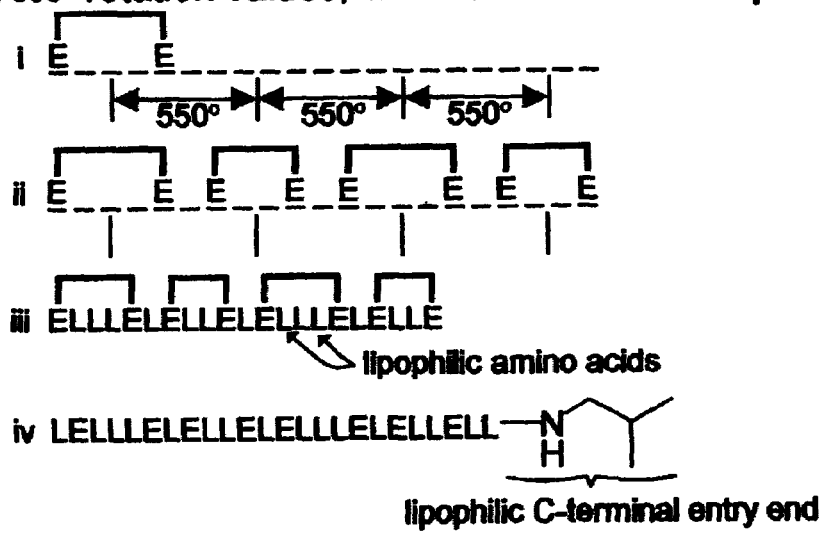
b) 600° rotation values, ELLLE acid pair type
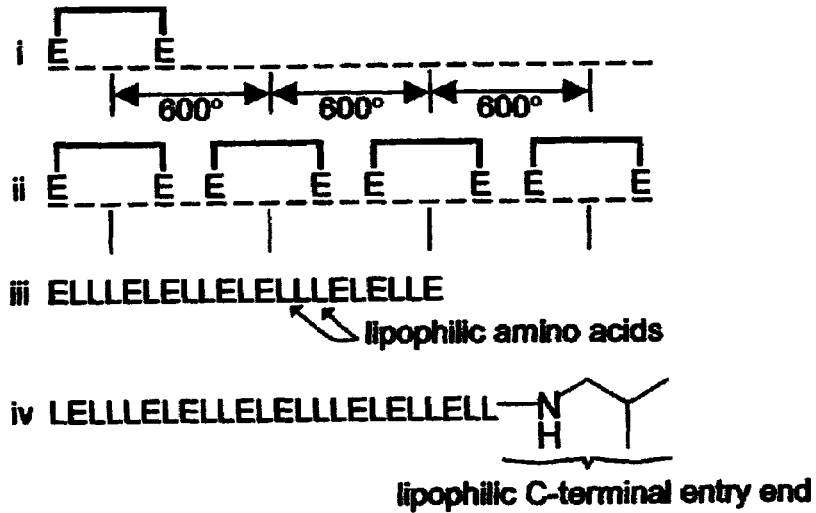

Figure 8.
Transporter peptide sequences, each with a single acid pair type
a) 550° axial rotation values
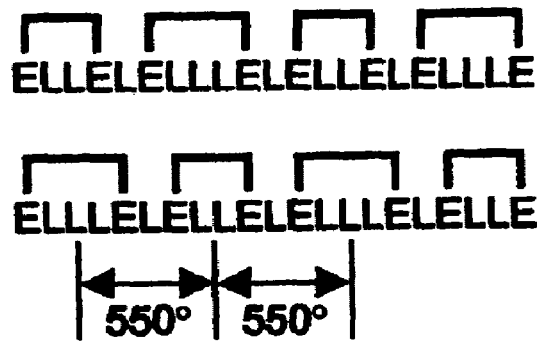
b) 600° axial rotation values
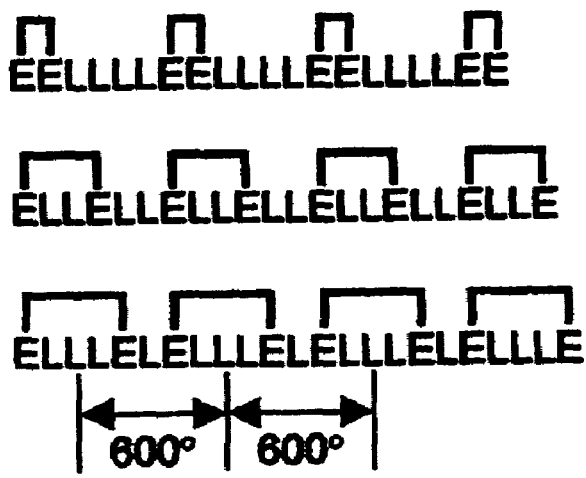

Figure 9a,b.
Transporter peptide sequences with mixed rotation values
a) alternating 500° and 550° rotation values
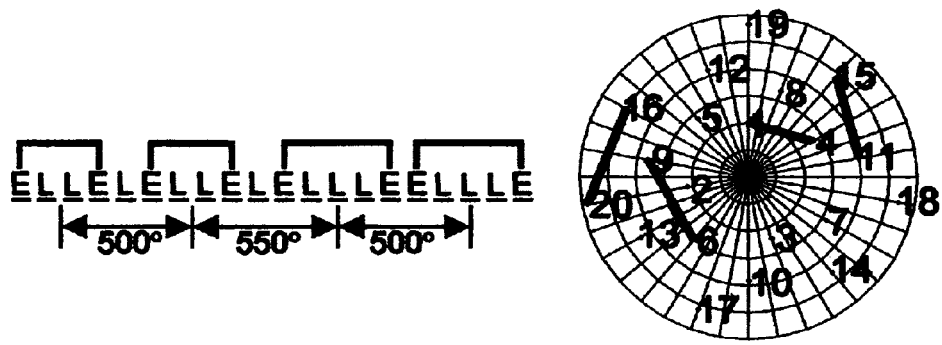
b) alternating 550° and 600° rotation values
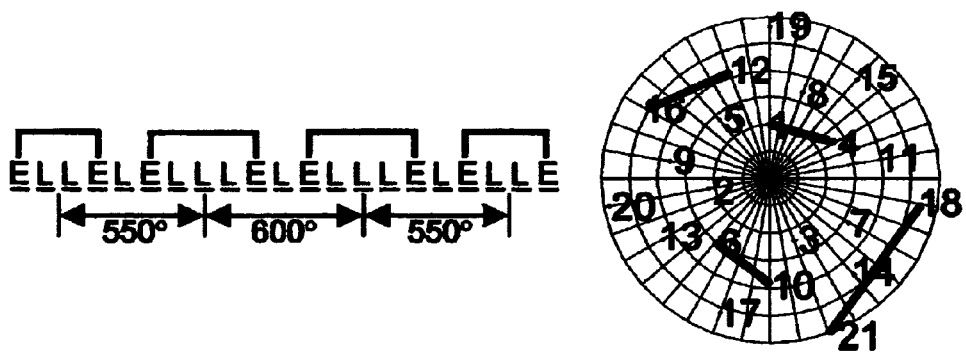

Transporter peptide sequences with mixed rotation values c) alternating 500° and 600° rotation values Figure 10a.
Transporter peptide sequences with EE acid pairs
mixed with ELLE and ELLLE acid pairs
a) EE acid pairs alternating with ELLE acid pairs
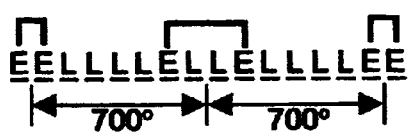 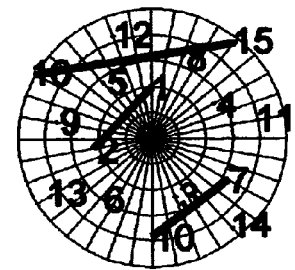
 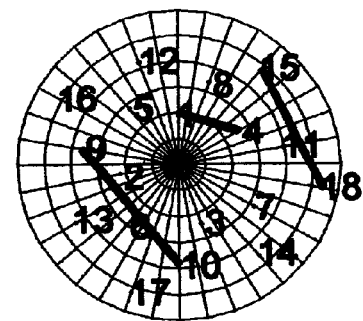

Figure 10b,c.
Transporter peptide sequences with EE acid pairs mixed with ELLE and ELLLE acid pairs
b) EE acid pairs alternating with ELLLE acid pairs
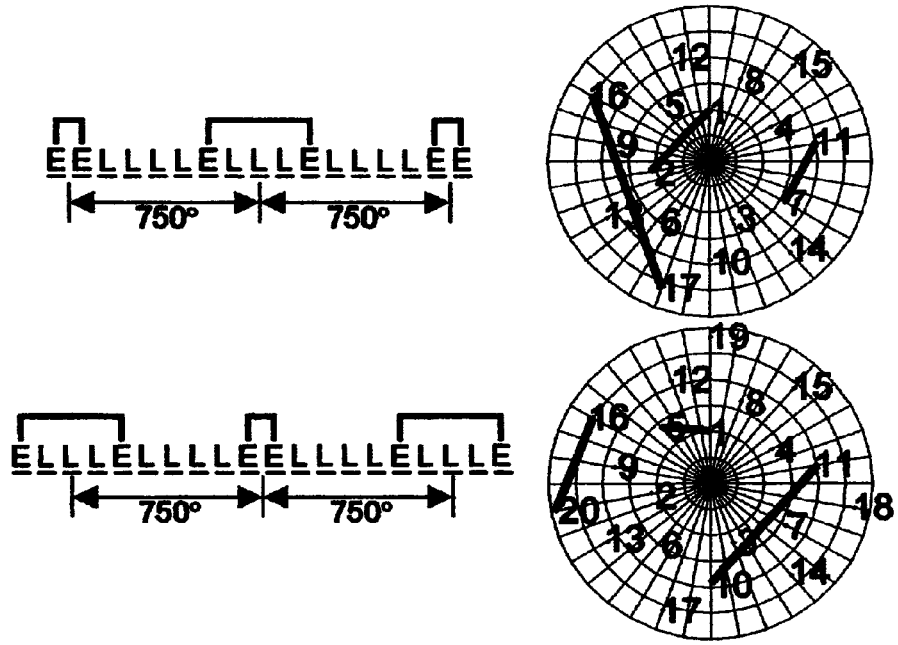
c) EE acid pairs alternating with both ELLE and ELLLE acid pairs
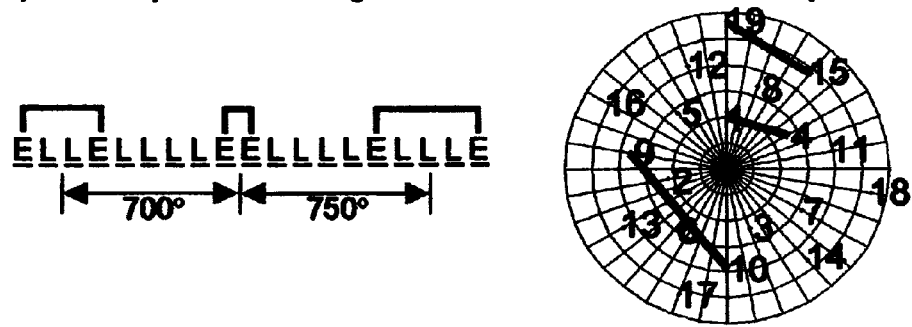

Representative transporter compositions

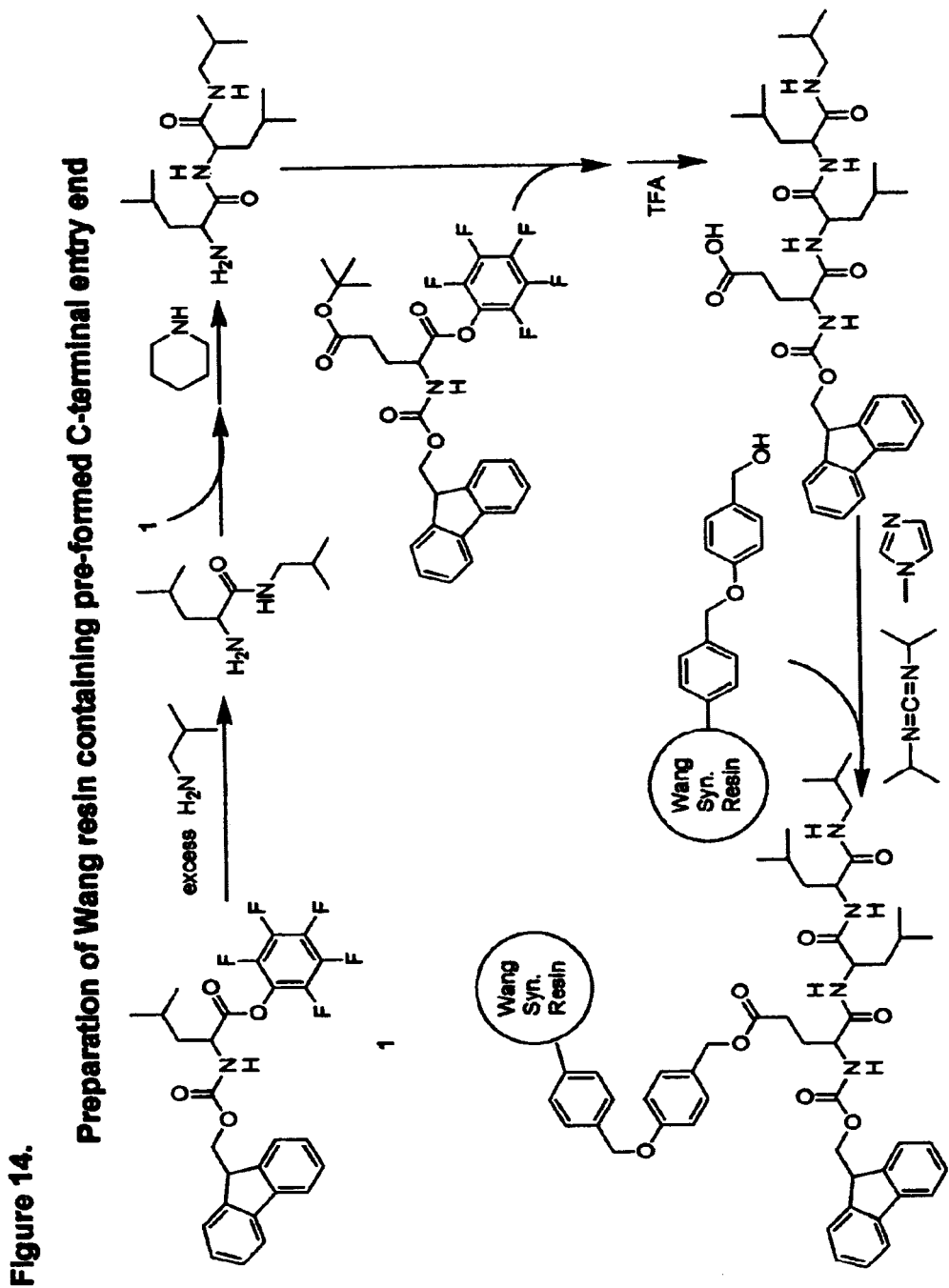
Figure 14. Preparation of Wang resin containing pre-formed C-terminal entry end Attachment of diagnostic cargo component to N-terminus of transporter peptide Attachment of therapeutic cargo component to N-terminus of transporter peptide

Attachment of a therapeutic cargo to C-terminus of transporter peptide

Incorporation of a precursor to a cargo component during peptide synthesis

Figure 17.
Representative transporter compositions for diagnostic application
a) Lower pE
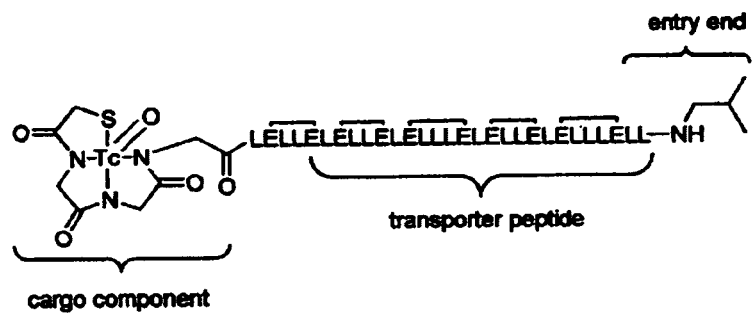
b) Higher pE
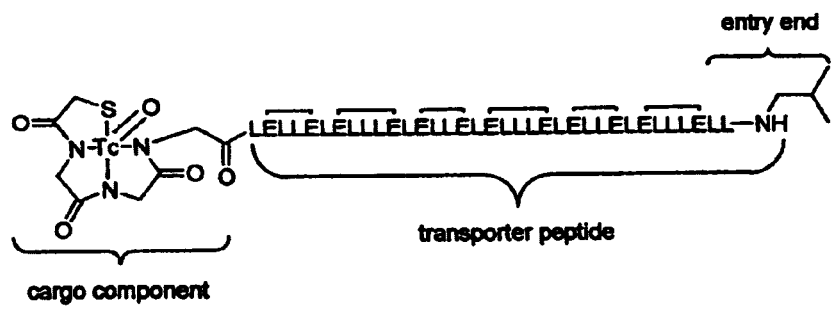

Figure 18.

Representative transporter compositions for therapeutic application a) Lower pE entry end $\underbrace{\phantom{XXXXXXXXXXXX}}_{\text{cargo component}}$ —LELLELELLELELELELELELELELELELELL—NH $\underbrace{\phantom{XXXXXXXXXXXX}}_{\text{transporter peptide}}$ b) Higher pE entry end $\underbrace{\phantom{XXXXXXXXXXXX}}_{\text{cargo component}}$ —LELLELELLELELLELELLELELLELELLLELL—NH $\underbrace{\phantom{XXXXXXXXXXXX}}_{\text{transporter peptide}}$

```
                            SEQUENCE LISTING

<160> NUMBER OF SEQ ID NOS: 47

<210> SEQ ID NO 1
<211> LENGTH: 16
<212> TYPE: PRT
<213> ORGANISM: human

<400> SEQUENCE: 1

Glu Leu Leu Glu Leu Glu Leu Leu Glu Leu Glu Leu Leu Glu Leu
1               5                   10                  15

<210> SEQ ID NO 2
<211> LENGTH: 16
<212> TYPE: PRT
<213> ORGANISM: human

<400> SEQUENCE: 2

Glu Leu Leu Leu Glu Leu Glu Leu Leu Glu Leu Glu Leu Leu Leu Glu
1               5                   10                  15

<210> SEQ ID NO 3
<211> LENGTH: 16
<212> TYPE: PRT
<213> ORGANISM: human

<400> SEQUENCE: 3

Glu Leu Leu Leu Glu Leu Glu Leu Leu Glu Leu Glu Leu Leu Leu Glu
1               5                   10                  15

<210> SEQ ID NO 4
<211> LENGTH: 16
<212> TYPE: PRT
<213> ORGANISM: human

<400> SEQUENCE: 4

Glu Leu Leu Glu Leu Glu Leu Leu Leu Glu Leu Glu Leu Leu Glu Leu
1               5                   10                  15

<210> SEQ ID NO 5
<211> LENGTH: 11
<212> TYPE: PRT
<213> ORGANISM: human

<400> SEQUENCE: 5

Glu Leu Leu Glu Leu Glu Leu Leu Leu Glu Leu
1               5                   10

<210> SEQ ID NO 6
<211> LENGTH: 11
<212> TYPE: PRT
<213> ORGANISM: human

<400> SEQUENCE: 6

Glu Leu Leu Leu Glu Leu Glu Leu Leu Glu Leu
```

```
1               5                    10

<210> SEQ ID NO 7
<211> LENGTH: 6
<212> TYPE: PRT
<213> ORGANISM: human

<400> SEQUENCE: 7

Glu Leu Leu Leu Glu Leu
1               5

<210> SEQ ID NO 8
<211> LENGTH: 16
<212> TYPE: PRT
<213> ORGANISM: human

<400> SEQUENCE: 8

Glu Leu Leu Leu Glu Leu Glu Leu Glu Leu Glu Leu Leu Leu Leu Glu
1               5                   10                  15

<210> SEQ ID NO 9
<211> LENGTH: 16
<212> TYPE: PRT
<213> ORGANISM: human

<400> SEQUENCE: 9

Glu Leu Leu Glu Leu Glu Leu Leu Glu Leu Glu Leu Leu Glu Glu Leu
1               5                   10                  15

<210> SEQ ID NO 10
<211> LENGTH: 30
<212> TYPE: PRT
<213> ORGANISM: human

<400> SEQUENCE: 10

Leu Glu Leu Leu Leu Glu Leu Glu Leu Glu Leu Glu Leu Leu Leu Leu
1               5                   10                  15

Glu Leu Glu Leu Leu Glu Leu Glu Leu Glu Leu Leu Leu Glu
            20                  25                  30

<210> SEQ ID NO 11
<211> LENGTH: 19
<212> TYPE: PRT
<213> ORGANISM: human

<400> SEQUENCE: 11

Leu Leu Glu Leu Leu Glu Glu Leu Glu Glu Leu Leu Glu Glu Glu Leu
1               5                   10                  15

Leu Glu Leu

<210> SEQ ID NO 12
<211> LENGTH: 14
<212> TYPE: PRT
<213> ORGANISM: human

<400> SEQUENCE: 12

Leu Leu Leu Leu Leu Leu Leu Leu Leu Leu Leu Leu Leu Leu
1               5                   10

<210> SEQ ID NO 13
<211> LENGTH: 24
<212> TYPE: PRT
<213> ORGANISM: human
```

```
<400> SEQUENCE: 13

Leu Leu Glu Leu Leu Leu Glu Leu Glu Leu Leu Glu Leu Glu Leu Leu
1               5                   10                  15

Leu Glu Leu Glu Leu Leu Glu Ala
            20

<210> SEQ ID NO 14
<211> LENGTH: 20
<212> TYPE: PRT
<213> ORGANISM: human

<400> SEQUENCE: 14

Leu Leu Glu Leu Leu Leu Glu Leu Glu Leu Leu Leu Glu Leu Glu Leu
1               5                   10                  15

Leu Leu Glu Leu
            20

<210> SEQ ID NO 15
<211> LENGTH: 9
<212> TYPE: PRT
<213> ORGANISM: human

<400> SEQUENCE: 15

Glu Leu Leu Glu Glu Leu Leu Leu Glu
1               5

<210> SEQ ID NO 16
<211> LENGTH: 7
<212> TYPE: PRT
<213> ORGANISM: human

<400> SEQUENCE: 16

Glu Glu Leu Leu Leu Glu Glu
1               5

<210> SEQ ID NO 17
<211> LENGTH: 9
<212> TYPE: PRT
<213> ORGANISM: human

<400> SEQUENCE: 17

Glu Leu Leu Glu Leu Glu Leu Leu Glu
1               5

<210> SEQ ID NO 18
<211> LENGTH: 10
<212> TYPE: PRT
<213> ORGANISM: human

<400> SEQUENCE: 18

Glu Leu Leu Leu Glu Glu Leu Leu Leu Glu
1               5                   10

<210> SEQ ID NO 19
<211> LENGTH: 10
<212> TYPE: PRT
<213> ORGANISM: human

<400> SEQUENCE: 19

Glu Leu Leu Glu Leu Glu Leu Leu Leu Glu
1               5                   10

<210> SEQ ID NO 20
```

```
<211> LENGTH: 10
<212> TYPE: PRT
<213> ORGANISM: human

<400> SEQUENCE: 20

Glu Leu Leu Leu Glu Leu Glu Leu Leu Glu
1               5                   10

<210> SEQ ID NO 21
<211> LENGTH: 8
<212> TYPE: PRT
<213> ORGANISM: human

<400> SEQUENCE: 21

Glu Glu Leu Leu Leu Leu Glu Glu
1               5

<210> SEQ ID NO 22
<211> LENGTH: 10
<212> TYPE: PRT
<213> ORGANISM: human

<400> SEQUENCE: 22

Glu Leu Leu Glu Leu Leu Glu Leu Leu Glu
1               5                   10

<210> SEQ ID NO 23
<211> LENGTH: 11
<212> TYPE: PRT
<213> ORGANISM: human

<400> SEQUENCE: 23

Glu Leu Leu Leu Glu Leu Glu Leu Leu Glu
1               5                   10

<210> SEQ ID NO 24
<211> LENGTH: 11
<212> TYPE: PRT
<213> ORGANISM: human

<400> SEQUENCE: 24

Glu Leu Leu Leu Glu Leu Leu Glu Leu Leu Glu
1               5                   10

<210> SEQ ID NO 25
<211> LENGTH: 24
<212> TYPE: PRT
<213> ORGANISM: human

<400> SEQUENCE: 25

Glu Leu Leu Leu Glu Glu Leu Leu Glu Leu Leu Glu Leu Glu Leu
1               5                   10                  15

Leu Leu Glu Leu Glu Leu Leu Glu
            20

<210> SEQ ID NO 26
<211> LENGTH: 24
<212> TYPE: PRT
<213> ORGANISM: human

<400> SEQUENCE: 26

Leu Glu Leu Leu Leu Glu Leu Glu Leu Leu Glu Leu Glu Leu Leu Leu
1               5                   10                  15

Glu Leu Glu Leu Leu Glu Leu Leu
```

<210> SEQ ID NO 27
<211> LENGTH: 23
<212> TYPE: PRT
<213> ORGANISM: human

<400> SEQUENCE: 27

Glu Leu Leu Leu Glu Leu Glu Leu Leu Glu Leu Glu Leu Leu
1               5                   10                  15

Glu Leu Glu Leu Leu Leu Glu
            20

<210> SEQ ID NO 28
<211> LENGTH: 32
<212> TYPE: PRT
<213> ORGANISM: human

<400> SEQUENCE: 28

Leu Glu Leu Leu Leu Glu Leu Glu Leu Leu Glu Leu Glu Leu Leu
1               5                   10                  15

Leu Glu Leu Glu Leu Leu Leu Glu Leu Glu Leu Leu Glu Leu Leu
            20                  25                  30

<210> SEQ ID NO 29
<211> LENGTH: 22
<212> TYPE: PRT
<213> ORGANISM: human

<400> SEQUENCE: 29

Glu Leu Leu Glu Leu Glu Leu Glu Leu Leu Glu Leu Glu Leu Glu
1               5                   10                  15

Leu Glu Leu Leu Leu Glu
            20

<210> SEQ ID NO 30
<211> LENGTH: 21
<212> TYPE: PRT
<213> ORGANISM: human

<400> SEQUENCE: 30

Glu Leu Leu Leu Glu Leu Glu Leu Leu Glu Leu Glu Leu Leu Glu
1               5                   10                  15

Leu Glu Leu Leu Glu
            20

<210> SEQ ID NO 31
<211> LENGTH: 20
<212> TYPE: PRT
<213> ORGANISM: human

<400> SEQUENCE: 31

Glu Glu Leu Leu Leu Leu Glu Glu Leu Leu Leu Leu Glu Glu Leu Leu
1               5                   10                  15

Leu Leu Glu Glu
            20

<210> SEQ ID NO 32
<211> LENGTH: 22
<212> TYPE: PRT
<213> ORGANISM: human

<400> SEQUENCE: 32

-continued

Glu Leu Leu Glu Leu Leu Glu Leu Leu Glu Leu Glu Leu Glu
1               5                   10                  15

Leu Leu Glu Leu Leu Glu
            20

<210> SEQ ID NO 33
<211> LENGTH: 23
<212> TYPE: PRT
<213> ORGANISM: human

<400> SEQUENCE: 33

Glu Leu Leu Leu Glu Leu Glu Leu Leu Glu Leu Glu Leu Leu Leu
1               5                   10                  15

Glu Leu Glu Leu Leu Leu Glu
            20

<210> SEQ ID NO 34
<211> LENGTH: 20
<212> TYPE: PRT
<213> ORGANISM: human

<400> SEQUENCE: 34

Glu Leu Leu Glu Leu Glu Leu Leu Glu Leu Glu Leu Leu Glu Glu
1               5                   10                  15

Leu Leu Leu Glu
            20

<210> SEQ ID NO 35
<211> LENGTH: 21
<212> TYPE: PRT
<213> ORGANISM: humn

<400> SEQUENCE: 35

Glu Leu Leu Glu Leu Glu Leu Leu Glu Leu Glu Leu Leu Leu Glu
1               5                   10                  15

Leu Glu Leu Leu Glu
            20

<210> SEQ ID NO 36
<211> LENGTH: 20
<212> TYPE: PRT
<213> ORGANISM: human

<400> SEQUENCE: 36

Glu Leu Leu Glu Leu Glu Leu Leu Glu Leu Leu Glu Leu Glu Leu
1               5                   10                  15

Glu Leu Leu Glu
            20

<210> SEQ ID NO 37
<211> LENGTH: 18
<212> TYPE: PRT
<213> ORGANISM: human

<400> SEQUENCE: 37

Glu Glu Leu Leu Leu Glu Glu Leu Leu Leu Leu Glu Glu Leu Leu
1               5                   10                  15

Glu Glu

<210> SEQ ID NO 38
<211> LENGTH: 16

<212> TYPE: PRT
<213> ORGANISM: human

<400> SEQUENCE: 38

Glu Glu Leu Leu Leu Leu Glu Leu Leu Glu Leu Leu Leu Glu Glu
1               5                   10                  15

<210> SEQ ID NO 39
<211> LENGTH: 18
<212> TYPE: PRT
<213> ORGANISM: human

<400> SEQUENCE: 39

Glu Leu Leu Glu Leu Leu Leu Glu Glu Leu Leu Leu Leu Glu Leu
1               5                   10                  15

Leu Glu

<210> SEQ ID NO 40
<211> LENGTH: 17
<212> TYPE: PRT
<213> ORGANISM: human

<400> SEQUENCE: 40

Glu Glu Leu Leu Leu Leu Glu Leu Leu Leu Glu Leu Leu Leu Glu
1               5                   10                  15

Glu

<210> SEQ ID NO 41
<211> LENGTH: 20
<212> TYPE: PRT
<213> ORGANISM: human

<400> SEQUENCE: 41

Glu Leu Leu Leu Glu Leu Leu Leu Glu Glu Leu Leu Leu Leu Glu
1               5                   10                  15

Leu Leu Leu Glu
            20

<210> SEQ ID NO 42
<211> LENGTH: 19
<212> TYPE: PRT
<213> ORGANISM: human

<400> SEQUENCE: 42

Glu Leu Leu Glu Leu Leu Leu Leu Glu Glu Leu Leu Leu Leu Glu Leu
1               5                   10                  15

Leu Leu Glu

<210> SEQ ID NO 43
<211> LENGTH: 28
<212> TYPE: PRT
<213> ORGANISM: human

<400> SEQUENCE: 43

Leu Glu Leu Leu Glu Leu Glu Leu Leu Glu Leu Glu Leu Leu Leu Glu
1               5                   10                  15

Glu Leu Leu Leu Glu Leu Glu Leu Leu Glu Leu Leu
            20                  25

<210> SEQ ID NO 44
<211> LENGTH: 30
<212> TYPE: PRT

-continued

```
<213> ORGANISM: human

<400> SEQUENCE: 44

Leu Glu Leu Leu Leu Glu Leu Glu Leu Leu Glu Leu Glu Leu Leu Leu
1               5                   10                  15

Glu Leu Glu Leu Leu Glu Leu Glu Leu Leu Leu Glu Leu Leu
            20                  25                  30

<210> SEQ ID NO 45
<211> LENGTH: 32
<212> TYPE: PRT
<213> ORGANISM: human

<400> SEQUENCE: 45

Leu Glu Leu Leu Leu Glu Leu Glu Leu Leu Leu Glu Leu Glu Leu Leu
1               5                   10                  15

Leu Glu Leu Glu Leu Leu Leu Glu Leu Glu Leu Leu Leu Glu Leu Leu
            20                  25                  30

<210> SEQ ID NO 46
<211> LENGTH: 29
<212> TYPE: PRT
<213> ORGANISM: human

<400> SEQUENCE: 46

Leu Glu Leu Leu Glu Leu Glu Leu Leu Glu Leu Glu Leu Leu Leu Glu
1               5                   10                  15

Leu Glu Leu Leu Glu Leu Glu Leu Leu Leu Glu Leu Leu
            20                  25

<210> SEQ ID NO 47
<211> LENGTH: 35
<212> TYPE: PRT
<213> ORGANISM: human

<400> SEQUENCE: 47

Leu Glu Leu Leu Glu Leu Glu Leu Leu Leu Glu Leu Glu Leu Leu Glu
1               5                   10                  15

Leu Glu Leu Leu Leu Glu Leu Glu Leu Leu Glu Leu Glu Leu Leu Leu
            20                  25                  30

Glu Leu Leu
        35
```

TRANSPORTER COMPOSITIONS AND METHODS FOR DETECTING AND KILLING CELLS IN ACIDIC AREAS OF TUMORS

RELATED PATENT APPLICATION

The present application is filed concurrently with an application entitled "Embedder Compositions and Methods for Detecting and Killing Cells in Acidic Areas of Tumors", Ser. No. 11/069,849, filed on 28 Feb. 2005, invented by applicant, and likewise assigned to GENE TOOLS, LLC.

FIELD OF THE INVENTION

The present invention relates to the use of transporter compositions for detecting or killing cells in acidic areas of tumors. At the neutral pH of normal tissues the transporter peptide of the composition of this invention exists in a poly-anionic form effective to repel from and not enter into cells. In acidic areas of tumors the transporter peptide converts to a non-ionic lipophilic form effective to cross cell membranes and carry a cargo component into cells.

BACKGROUND AND RELATED ART

Tumors larger than microscopic size have inadequate and abnormal vasculature. As a consequence, areas of tumors that are more than a few tens of microns from a capillary are generally hypoxic. Cells in such hypoxic areas of tumors either die or convert to anaerobic metabolism which results in their excreting lactic acid. Because of the poor circulation in tumors, that excreted lactic acid builds up in the interstitial space in hypoxic areas of tumors.

There are two important consequences of this process.

1) While the pH in the interstitial space in normal tissues ranges from about 7.2 to 7.5, the interstitial space in hypoxic areas of tumors is acidic, with pH ranging from as low as about 6.0 in areas most distant from capillaries, up to about 7.0 closer to capillaries.

2) While tumor cells in close proximity to capillaries are characterized by high metabolic rates and fast cell division, the tumor cells in acidic areas more distant from capillaries have lower metabolic rates and are slower-dividing or non-dividing. The slow-dividing and non-dividing tumor cells are referred to as quiescent.

Conventional cancer therapies, including chemotherapy and radiation, are generally fairly effective in killing fast-dividing cells, but because conventional cancer therapies are explicitly selected on the basis of their ability to spare slow-dividing and non-dividing cells typical of most normal tissues, said cancer therapies are also relatively ineffective against slow-dividing and non-dividing quiescent tumor cells. As a consequence, cancer treatments typically kill predominantly the fast-dividing cells of a tumor, while sparing the quiescent cells of the tumor. The initial killing of the fast-dividing tumor cells causes the tumor to go into remission. After those killed cells have been disposed of by the body's normal cleanup processes, all too often the treatment-resistant quiescent cancer cells in the hypoxic areas of the tumor slowly regain access to adequate oxygen, nutrients, and waste disposal, thus allowing them to revert to high metabolic rate and fast cell division. Reversion of the previously-quiescent cancer cells manifests as the dreaded relapse that so often kills cancer patients.

To achieve more effective treatment of tumors it is desirable to have a means for sensitive detection of quiescent cancer cells in virtually all tumors. Also desired is to have a broadly effective means for selectively killing those treatment-resistant quiescent cancer cells without concomitant killing of cells in normal tissues.

1. Related Art

There are two distinct types of compositions for detecting and treating cells in acidic areas of tumors: embedder compositions and transporter compositions. Compositions of the embedder type position their cargos on the outer surface of cells, as illustrated in Comparative FIG. 1a [RELATED ART]. In contrast, compositions of the transporter type of the instant invention carry their cargos into the cytosol of cells, as illustrated in FIG. 1.

Embedder compositions are described in a co-submitted and co-pending patent application by applicant cited supra and relating to embedder compositions and methods. Said embedder compositions repel from cells at the pH in normal tissues, but embed into membranes and thereby position their cargos on the outer surface of cells in acidic areas of tumors. Embedder compositions contain cargos which are effective on external cell surfaces. Such cargos can be relatively large and/or polar because it is not necessary to pull them across the cell membrane. One important difference between embedder compositions of said co-pending patent application and the transporter compositions of the instant invention is that for therapeutic application the cargo of the embedder composition can be designed to exploit a component of the body's natural extracellular cell-killing machinery, such as phagocytic cells or the innate immune system.

2. Prior Art

In the mid-1990s applicant pioneered the development of transporter peptides designed to transport substances from a low-pH environment across a lipid layer to a higher-pH aqueous compartment. The original transporter peptides are described and claimed in U.S. Pat. No. 6,030,941, issued to Summerton and Weller and assigned to AVI BioPharma, Inc. When 941 was filed in 1997 it was believed by applicant that structures with the highest practical pH of transition (pT) had been devised and were claimed in 941. Those high-pT peptides comprise peptides containing either of the two core repeating sequences [LELLE]n or [ELLLE]n. Furthermore, results from early octanol/buffer partitioning studies suggested that those high-pT peptides should be adequate for delivering substances into virtually all cells in acidic areas of tumors.

However, in subsequent studies of entry of transporter peptides into mammalian cell membranes and into mammalian cells at 37 degrees C., applicant discovered that the high-pT peptides claimed in 941 only enter cell membranes at a substantially lower pH than would be expected on the basis of the early partitioning results. The implication of this new finding is that the early high-pT peptides claimed in 941 will likely be effective only in the most acidic areas of tumors most distant from capillaries. This leaves a substantial portion of the acidic areas of tumors undetected or untreated by transporter compositions utilizing such prior art peptide sequences. This is illustrated in Comparative FIG. 2a [PRIOR ART].

The discovery of the limitations of the high-pT transporter peptides claimed in 941 led applicant to search for transporter peptide sequences having even higher pT values, which it was hoped would be effective to enter cells in a substantially wider range of acidic areas of tumors. Those efforts led to the discovery by applicant of a number of improved transporter peptide sequences patentably distinct from the claims of 941. The improved transporter peptide sequences disclosed and claimed herein have been found to enter mammalian cells at appreciably higher pH values and so should allow one to effectively detect or treat a much larger portion of the acidic areas of tumors, as illustrated in FIG. 2.

Table 1 lists key differences between the prior art transporter peptides described and claimed in 941 and the newly devised improved transporter peptides of the instant invention. These properties will be further described in the detailed description of the invention.

TABLE 1

| Property | Prior Art (941) | Current Invention |
| --- | --- | --- |
| acid side chain content in core peptide sequence: | 40% or more | less than 40% |
| acid side chains selected from: | glutamic and aspartic | glutamic |
| average of axial rotations between pairs: | 500 degrees or less | more than 500 degrees |

Table 2 illustrates these differences for representative core transporter peptide sequences.

TABLE 2

| Property | Prior Art (941) | Current Invention |
| --- | --- | --- |
| core repeating sequence | [LELLE]n (40% E) | [ELLELELLLEL]n (36% E) |
| axial rotation between pairs | 500 degrees | 550 degrees |
| core repeating sequence | [ELLLE]n (40% E) | [ELLLELELLEL]n (36% E) |
| axial rotation between pairs | 500 degrees | 550 degrees |
| core repeating sequence | | [ELLLEL]n (33% E) |
| axial rotation between pairs | | 600 degrees |

While these differences between the prior art (941) and the current invention may appear modest, because of the typical pH distribution in tumors the improved peptides of the current invention are expected to afford a substantial increase in diagnostic sensitivity, and a dramatic improvement in therapeutic efficacy (when used in combination with conventional cancer therapy to kill the fast-dividing cells of the tumor), as illustrated in Comparative FIG. 2a [PRIOR ART] and FIG. 2.

SUMMARY OF THE INVENTION

To address the problem of selectively detecting and treating quiescent cancer cells in hypoxic areas of tumors, applicant has devised improved transporter compositions which are designed to repel from cells in normal tissues, but to transport into the cytosol of cells in a broad range of acidic areas of tumors. As illustrated in FIG. 3, when these improved transporter compositions are introduced into the body, if a tumor larger than microscopic size is present, a portion of the introduced dose will transport into cells in acidic areas of said tumor, with the remainder of the introduced dose being rapidly excreted from the body. When the composition is to be used for detecting tumors, it includes a cargo component suitable for detecting the composition. When the composition is to be used for treating the quiescent cells of tumors it includes a cargo component effective for killing the cells containing the composition.

The transporter composition of this invention includes two key components: a transporter peptide which repels from cells at neutral pH, but transports into cells in acidic areas of tumors; and, a cargo component which can be pulled across cell membranes by the transporter peptide, and which is effective for detecting or killing cells into which the transporter composition has entered.

In one aspect of the invention, a transporter composition provides a means for delivering a cargo into cells in acidic areas of tumors, without concomitant delivery into cells in areas of normal pH elsewhere in the body. This selectivity is achieved by use of a transporter peptide sequence which contains properly positioned carboxylic acid pairs interspersed with lipophilic amino acids.

The invention further includes a diagnostic method consisting of introducing one or more transporter compositions into a patient, and particularly a human patient, for the purpose of detecting any tumors which are present and which have acidic areas. Typically about 1 to about 24 hours after introducing the transporter composition (to allow clearance of extracellular transporter composition through the kidneys) the patient is scanned to detect the presence and position of any transporter composition within cells in acidic areas of tumors. For such applications the transporter composition includes a cargo which can be readily detected by methods known and practiced in the medical diagnostics art. Cargos for this purpose include fluors, radioisotopes, contrast agents, and the like.

The invention further includes an enhanced diagnostic method which additionally entails introducing into the patient a substance, such as glucose, which is effective to temporarily further reduce the pH in hypoxic areas of tumors.

The diagnostic method of the present invention also includes methods for minimizing re-uptake of transporter composition by the kidneys. These methods include treating the patient with a substance to minimize endocytotic uptake of peptides in the proximal tubules, and treating the patient with a substance to temporarily render the urine slightly alkaline.

In another aspect, the invention includes a therapeutic method consisting of introducing one or more transporter compositions into a patient, and particularly a human patient, for the purpose of killing cells in acidic areas of any tumors which are present. For such applications, the transporter composition includes a cargo which can kill cells. Cargos for this purpose include such agents as radioisotopes, intracellular toxins, and other cell-killing agents known in the cancer therapy art. The therapeutic method of the invention, for killing quiescent cancer cells in acidic areas of tumors, is preferably carried out in combination with conventional radiation or chemotherapy known in the art, for the purpose of also killing the fast-dividing cells of tumors.

The present invention further includes an enhanced therapeutic method which additionally entails introducing into the patient a substance, such as glucose, which is effective to temporarily further reduce the pH in hypoxic areas of tumors.

The therapeutic method of the invention also includes methods for minimizing re-uptake of transporter composition by the kidneys. These methods include treating the patient with a substance to minimize endocytotic uptake of peptides in the proximal tubules, and treating the patient with a substance to temporarily render the urine slightly alkaline.

Comparative FIG. 1a (RELATED ART) illustrates the embedder mode of action by embedder compositions in applicant's co-pending patent application.

Figure 2:
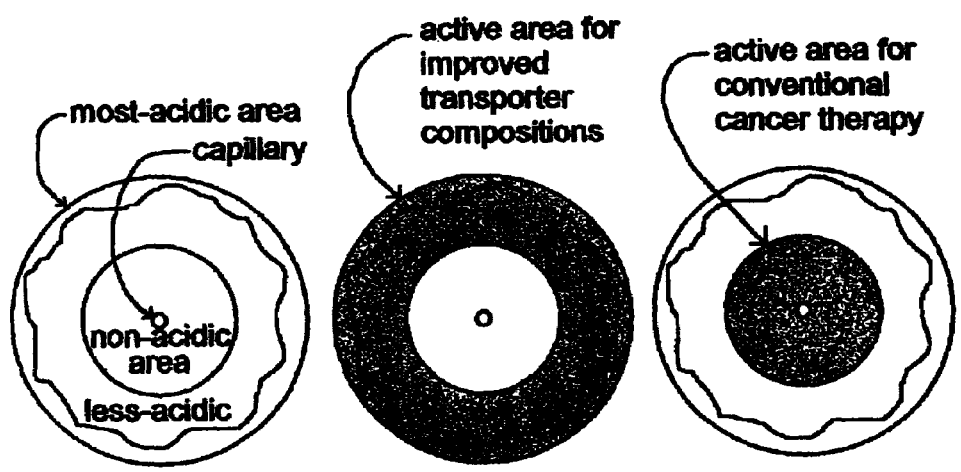

FIG. 2 illustrates the expected area of activity of improved transporter compositions of the instant invention.

Comparative FIG. 2a (PRIOR ART) illustrates the expected area of activity of prior art transporter compositions claimed in U.S. Pat. No. 6,030,941.

Figure 3:
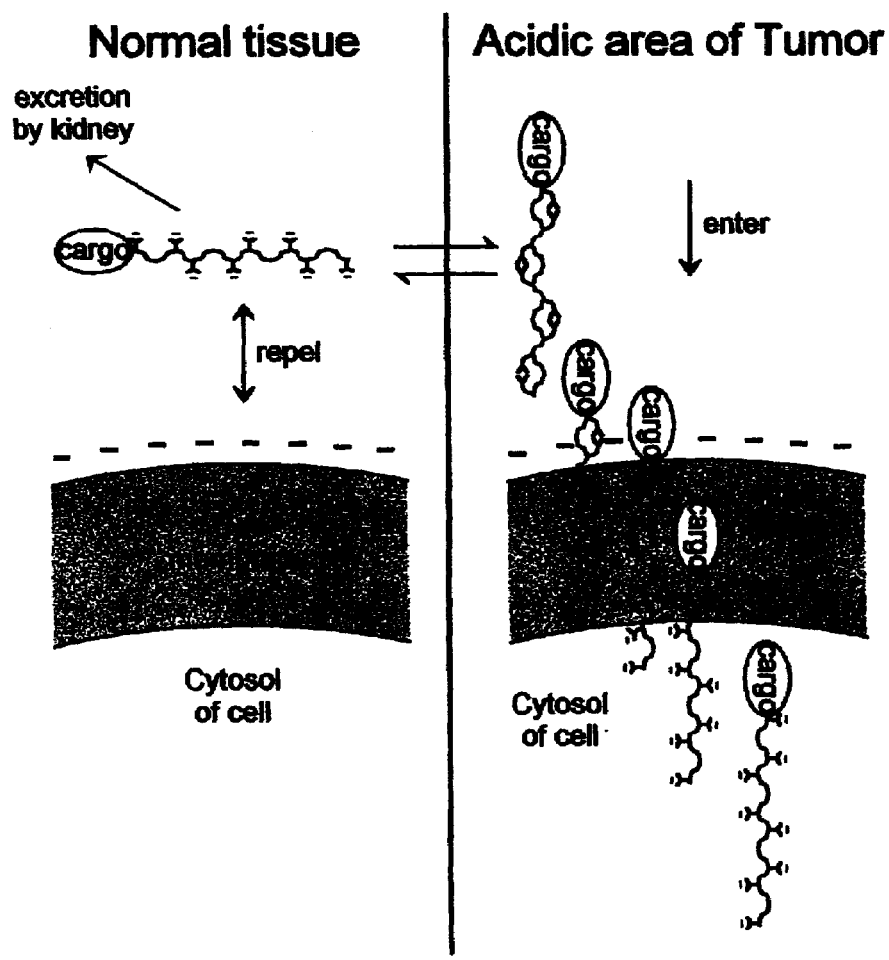

FIG. 3 illustrates a transporter composition repelling from a normal cell and entering a tumor cell.

FIG. 4 depicts a double-hydrogen-bonded acid pair structure.

FIG. 5 shows axial distribution plots of acid pairs.

FIG. 6 shows key structural features for selecting transporter peptide sequences.

FIG. 7 demonstrates the graphical selection of transporter peptide sequences.

FIG. 8 shows transporter peptide sequences, each with a single acid pair type.

Figure 9C:
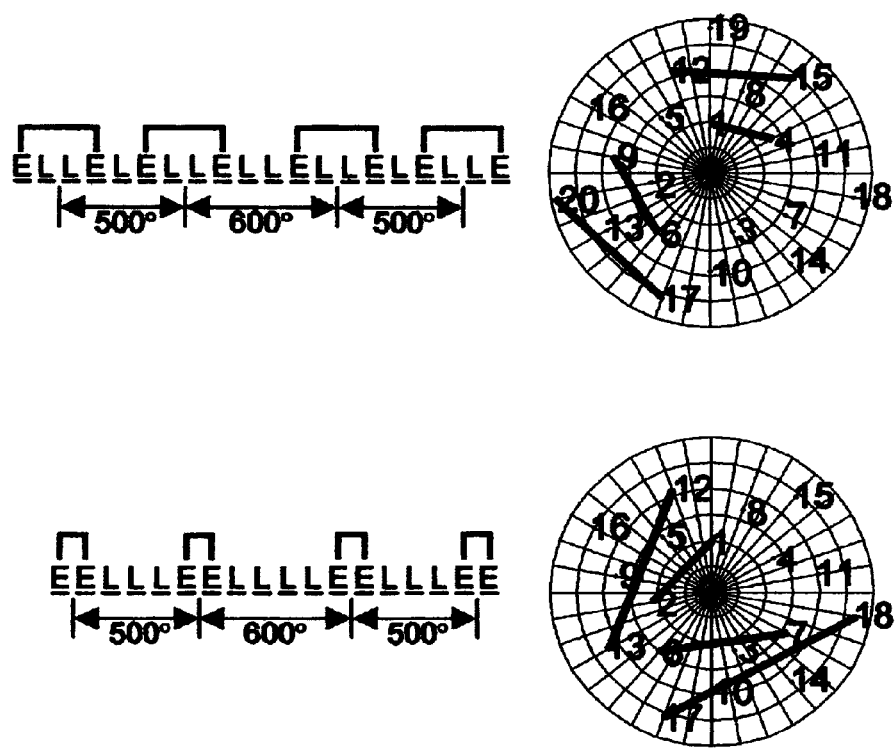

FIG. 9 shows transporter peptide sequences with mixed rotation values.

FIG. 10 shows transporter peptide sequences with EE acid pairs mixed with ELLE and ELLLE acid pairs.

Figure 11:
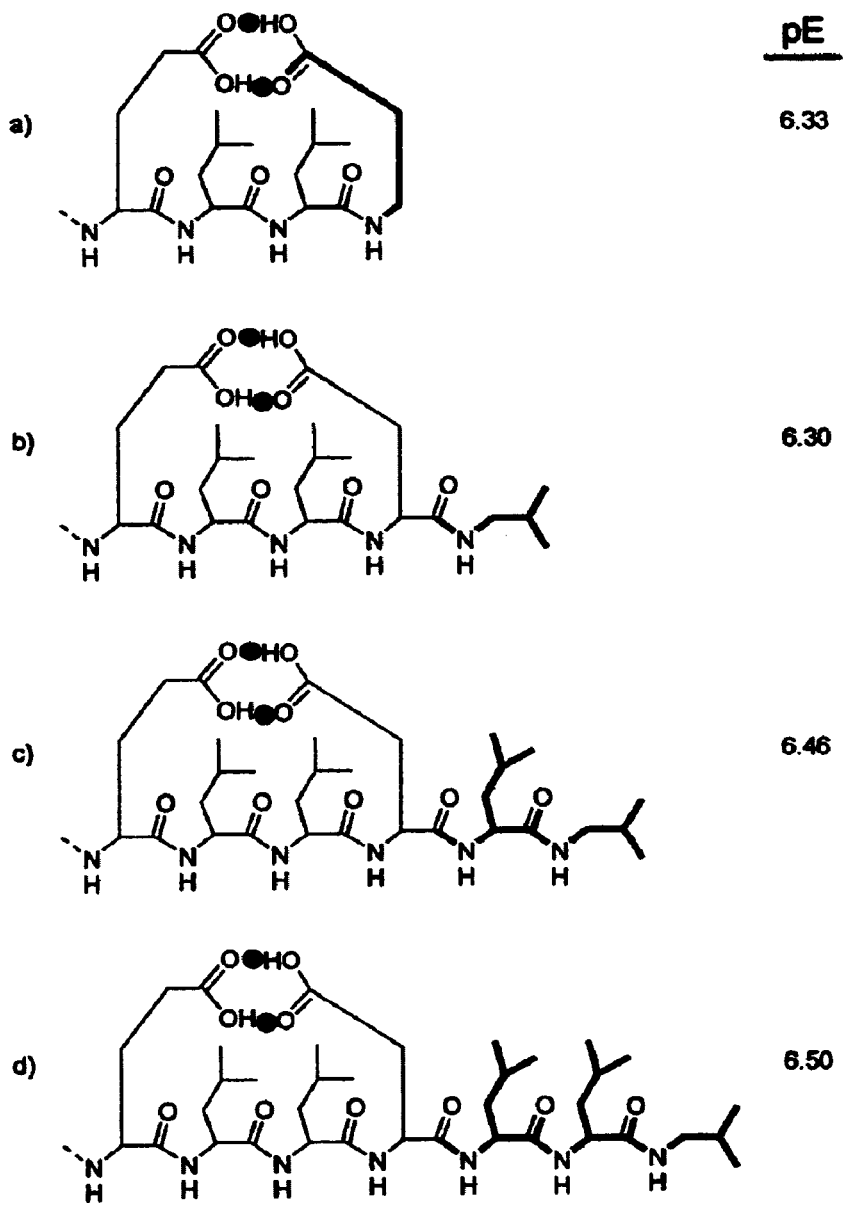

FIG. 11 shows C-terminal entry ends of transporter peptides.

Figure 12:
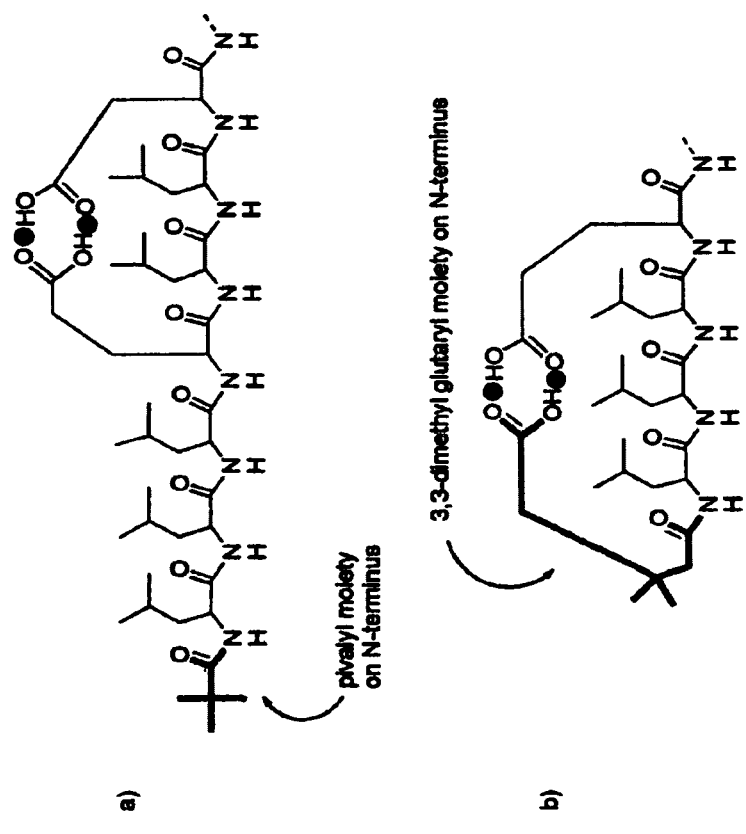

FIG. 12 shows N-terminal entry ends of transporter peptides.

Figure 13:
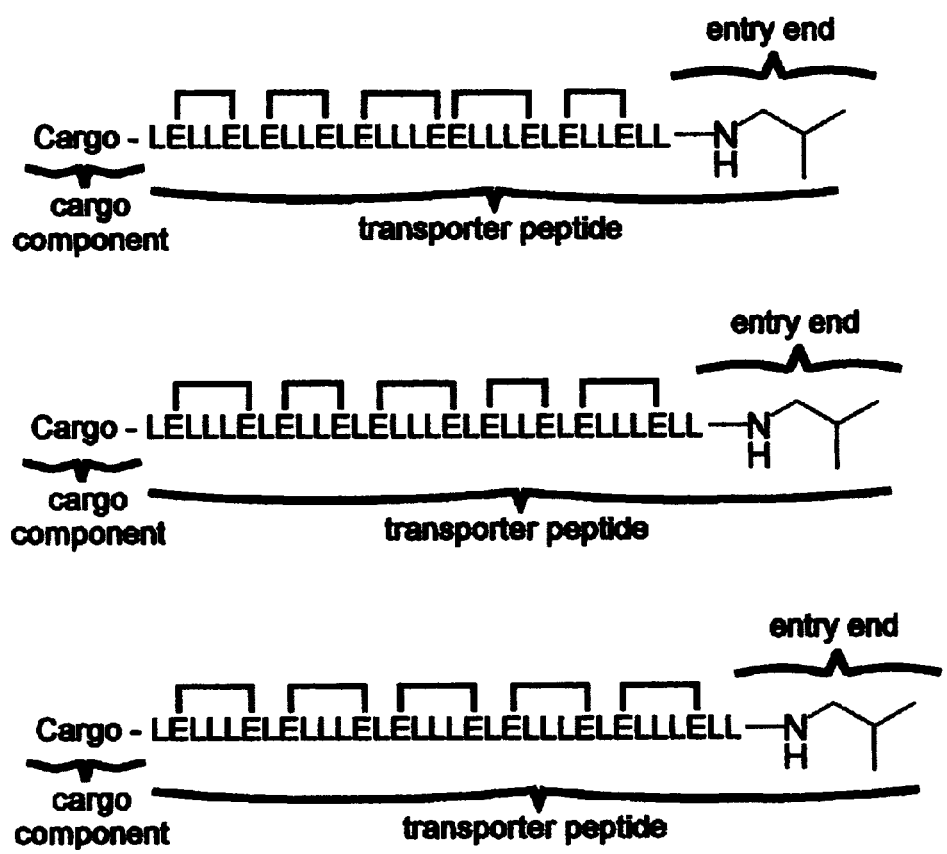

FIG. 13 shows representative transporter compositions.

FIG. 14 depicts the preparation of Wang resin containing a pre-formed C-terminal entry end.

FIG. 15 depicts attachment of cargo components to N-terminus of transporter peptide.

FIG. 16 depicts attachment of cargo components to C-terminus of transporter peptide.

FIG. 17 shows representative transporter compositions for diagnostic application.

FIG. 18 shows representative transporter compositions for therapeutic application.

DEFINITIONS USED IN THIS INVENTION

The terms used herein have the following specific meanings, unless otherwise noted.

"Transporter composition" means a composition which includes both: a) a transporter peptide that is poly-anionic at neutral pH, but converts in an acidic area of a tumor to a non-ionic lipophilic form which is effective to transport across a cell membrane; and, b) a cargo component which can be pulled across a cell membrane by said transporter peptide in an acidic area of a tumor.

"Precursor form of the transporter composition" means a composition which includes both: a) a transporter peptide that is poly-anionic at neutral pH, but converts in an acidic area of a tumor to a non-ionic lipophilic form which is effective to transport across a cell membrane; and, b) a precursor of a cargo component, where said precursor is reactive toward a substance such that when said precursor and said substance are contacted they form a cargo component which can be pulled across a cell membrane by the transporter peptide in acidic areas of a tumor, and which is effective for detecting or killing cells into which the transporter composition has entered.

"Prior art transporter composition" means a transporter composition relating to U.S. Pat. No. 6,030,941 wherein the core transporter peptide sequence of said transporter peptide comprises at least 40% acid side chains, and has an average of the axial rotations between acid pairs which is no more than 500 degrees.

"Improved transporter composition" means a transporter composition of the instant invention wherein the core transporter peptide sequence of the transporter peptide comprises less than 40% acid side chains, and has an average of the axial rotations between acid pairs which is more than 500 degrees, and wherein the cargo component is effective for detecting or killing cells into which the transporter composition has entered.

"Embedder composition" means a composition which includes both: a) an embedder peptide which repels from cells at neutral pH, but embeds in cell membranes in acidic areas of tumors; and, b) a cargo component which prevents passage across cell membranes and which is effective for detecting or killing cells in whose membranes the embedder peptide is embedded.

"Transporter peptide" means a transporter peptide sequence, with a lipophilic entry end, which is polyanionic at the pH in normal tissues, but converts to a predominantly non-ionic lipophilic form effective to enter cells in acidic areas of tumors.

"Core transporter peptide sequence" means that portion of the transporter peptide from the center point of the acid pair closest to the N-terminal end of the peptide and extending to the center point of the acid pair closest to the C-terminal end of the peptide.

"Transporter sequence" means the amino acid sequence of the transporter peptide. Amino acid sequences presented herein follow the standard convention of the N-terminal amino acid starting on the left and the C-terminal amino acid ending on the right.

"Amino acid sequence motif" means a specific short amino acid sequence which comprises a portion of a complete transporter peptide. Two novel amino acid sequence motifs which are particularly preferred as segments of improved transporter peptides are: . . . ELLELELLLELELLEL . . . and . . . ELLLELELLLELELLLE . . .

"Acid pair" means a pair of side chain carboxylic acids in a peptide sequence, where there are zero, two, or three amino acids intervening in the peptide backbone between the side chains of the pair, and which under acidic conditions the carboxyls of the acid pair form a double-hydrogen-bonded carboxylic acid pair structure when the peptide is in an alpha helical conformation as illustrated in FIG. 4.

"Lipophilic amino acid" (also designated as "L") means lipophilic amino acids, at least 90% of which are selected from the group consisting of: leucine, isoleucine, norleucine and methionine.

"L" means a lipophilic amino acid.

"Entry end" means the structural modifications at one terminus of the transporter peptide which, at a pH present or achievable in acidic areas of tumors, serve to dispose of the terminal ionic moiety typical of peptides, and render that peptide end sufficiently lipophilic to initiate entry into cell membranes.

"pH of transition" (pT) means the pH at which half of the transporter peptides are in the buffer phase and half are in the octanol phase in the partitioning assay as described in Example 5.

"pH of entry" (pE) means the pH at which half of the transporter peptides have entered cell membranes in the membrane binding assay described in Example 6.

"Cargo component" means a substance which can be pulled across cell membranes by the transporter peptide, and which is effective for detecting or killing the cell which it has entered. The cargo component includes one or more cargos.

"Cargo" means a substance effective for detecting or killing the cells which the transporter composition has entered.

"Diagnostic moiety" means a cargo effective for detecting the cells which the transporter composition has entered.

"Therapeutic moiety" means a cargo effective for killing the cells which the transporter composition has entered.

"Tumor" means a cancerous mass which contains hypoxic/acidic areas. "Tumor", as used herein is also commonly referred to as a malignancy, or as a neoplasm, or as a malignant neoplasm, or as a solid cancer.

DETAILED DESCRIPTION OF PREFERRED EMBODIMENTS

I. Structure and Function of Improved Transporter Composition

The transporter composition of the instant invention includes both a transporter peptide and a cargo component. The transporter peptide has an amino acid composition and sequence and a lipophilic entry end such that at about pH 7.2 and above the transporter peptide is poly-anionic, soluble in aqueous solution, and repels from negatively charged cell surfaces. At a lower pH present in acidic areas of tumors, ranging from about pH 6.0 to about 7.0, the transporter peptide converts to a largely non-ionic lipophilic form which is effective to cross cell membranes and enter the higher-pH cytosol of the cell. The cargo component includes one or more cargo moieties which can be pulled across the cell membrane by the transporter peptide. Said cargo component is effective for detecting or killing cells into which the transporter composition has transported.

When these transporter compositions are introduced into the body, if a tumor larger than microscopic size is present, a portion of the introduced dose will transport into cells in acidic areas of the tumor, with the remainder of the dose being excreted from the body, as illustrated in FIG. 3. When the composition is to be used for detecting tumors, it includes a cargo component effective for detecting the cells it has entered. When the composition is to be used for treating tumors, it includes a cargo component effective for killing the cells it has entered.

A. Transporter Peptide of Transporter Composition

1. Design Challenges for Transporter Peptide

A key requirement in designing a transporter composition effective for detection or treatment of cells in acidic areas of tumors is to assure that the transporter peptide of said composition will carry a sufficient number of negative charges at the pH present in normal tissues (about pH 7.2 and above) to assure adequate aqueous solubility and repulsion from the anionic surface of cell membranes. Then at a pH present in hypoxic areas of tumors, typically in the range of about pH 6.0 to about 7.0, the transporter peptide must convert to a predominantly non-ionic lipophilic form effective to pass through cell membranes into the higher-pH cytosolic compartment of the cell. In typical peptides such transitions between anionic and non-ionic forms, mediated primarily by carboxylic acid side chains of glutamic and aspartic acids, are fairly broad, generally with 80% of the transition occurring over 1.0 pH unit, and said transitions generally occur in a pH range centered around pH 4.5. The challenges that must be met in designing an effective transporter peptide are:

a) to change the center point of the transition between anionic and non-ionic forms from around pH 4.5 in typical peptides up to about pH 6.2 to 6.9 for the transporter peptide, and preferably to about 6.5 to about 6.9;

b) to make that transition substantially sharper than in typical peptides, preferably sharpening that transition so that about 80% of the transition occurs within a range of less than about 0.5 pH unit; and, c) to render the non-ionic free acid form of the carboxylic acid moieties considerably less polar than is typical in nearly all peptides and proteins.

2. Length of Transporter Peptide

Experimental work carried out in support of this invention shows that the transporter peptide should be at least about 16 amino acids in length in order to be effective for entering into the membranes of cells in acidic areas of tumors. However, when the transporter peptide is shorter than the thickness of the cell membrane (about 33 to 36 Angstroms, which corresponds to peptide lengths of 22 to 24 amino acids) such transporter peptides can only be used with cargos which are quite lipophilic and so provide little resistance to passage across the cell membrane. An example of such a lipophilic cargo, suitable for killing cells which it enters, is Cytochalasin B. Cytochalasin B kills cells by inhibiting microtubule formation.

Figure 1:
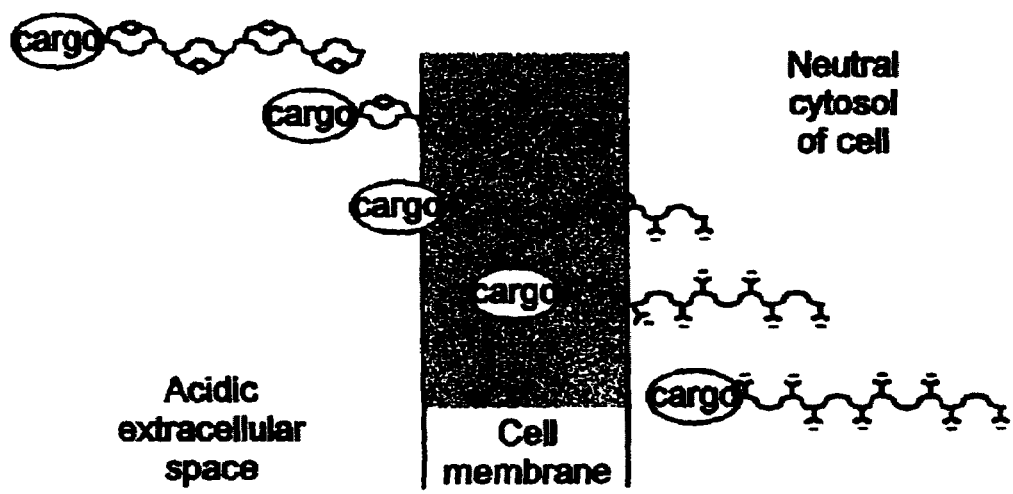
FIG. 1 illustrates the transporter mode of action by improved transporter compositions of the instant invention.

For transporter compositions where the cargo affords significant resistance to passage across a cell membrane, the transporter peptide should generally be at least as long as the membrane is thick, or about 22 to 24 amino acids in length, but preferably longer. The extra length over the thickness of the membrane is desirable because with such longer transporter peptides the entry end begins to enter the higher-pH cytosolic compartment while the segment of the peptide distal to the entry end, in its non-ionic lipophilic form, is still in the process of entering the membrane from the acidic exterior of the cell. When the first acid pair proximal to the entry end enters the higher-pH cytosol, the carboxyl moieties of that acid pair will separate and ionize. This ionization and attendant solvation serves to pull the transporter peptide further into the cytosol, resulting in even more acid pairs of the peptide contacting the higher-pH cytosol. This progressive entry of the peptide, driven by sequential ionization and solvation of the entering acid pairs, serves to pull the cargo through the cell membrane into the cytosol of the cell, as illustrated in FIGS. 1 and 3.

Experimental findings show that the pH at which transporter peptides of suitable sequence convert between their poly-anionic hydrophilic form and their non-ionic lipophilic form increases with increasing length. Therefore, increasing the length of the transporter peptide also serves as a means for raising the pH at which the transporter peptide will enter cells. However, ease of preparation and cost factors argue for a practical upper limit of about 50 amino acids in length for the transporter peptide.

3. Amino Acid Composition of Transporter Peptide

The transporter peptide is composed of two types of amino acids. Amino acids of one type have a lipophilic side chain, and amino acids of the other type have a carboxylic acid side chain.

Amino acids having a lipophilic side chain are referred to as lipophilic amino acids, and in peptide sequences they are designated with the single letter L. At least 90%, and preferably 100% of the lipophilic amino acids in a given transporter peptide should be selected from the group consisting of: leucine, isoleucine, norleucine and methionine. From the standpoint of ease of assembly into peptides, commercial availability, and cost, leucine is generally the preferred lipophilic amino acid.

The numbers of lipophilic amino acids relative to the numbers of carboxylic acid side chains in the core transporter peptide sequence are tabulated below, where the core transporter peptide sequence is defined as those amino acids extending from the mid-point of the acid pair closest to the N-terminus to the mid-point of the acid pair closest to the C-terminus of the transporter peptide.

| Number carboxylic acid side chains | Number of lipophilic amino acids (L) |
|---|---|
| 6 | more than 9 |
| 8 | more than 12 |
| 10 | more than 15 |
| 12 | more than 18 |

Amino acids having a carboxylic acid side chain, other than the one closest to the entry end, should be glutamic acid (single letter designation: E), but not aspartic acid (single letter designation: D). The carboxylic acid moiety closest to that peptide terminus designed to initiate entry into cell membranes (designated the "entry end") may be the side chain of glutamic acid or may be another carboxylic acid-containing side chain having a structure effective to form a double-hydrogen-bonded acid pair with a nearby glutamic acid side chain in the transporter peptide sequence, such as illustrated in FIGS. 11a and 12b.

4. Acid Pairs of Transporter Peptide

Some years ago it was discovered by applicant that with certain specific separations between two carboxylic acid side chains of a peptide existing in an alpha helical conformation, in aqueous solution under mildly acidic conditions those two carboxylic acids can cooperatively deionize and form a non-ionic double-H-bonded acid pair structure which serves to mask the polar sites of the two carboxylic acids, as illustrated in FIG. 4a. Carboxylic acid pairs with these specific separations are designated "acid pairs" and are defined supra. When a suitable number of such acid pairs are present and properly positioned along the peptide backbone, then in combination with intervening amino acids having appropriate lipophilic side chains, on acidification the resultant peptide can undergo a surprisingly sharp transition to a non-ionic lipophilic form at a pH up to about 2 pH units higher than the pH where typical carboxylic acids of peptides transition between their anionic and free-acid forms. It is the hydrogen-bond-mediated masking of the polarity of carboxylic acid moieties in these acid pairs which is essential for generating sufficient lipophilicity for entry of transporter peptides into membranes at a pH present or achievable in acidic areas of tumors. Because of constraints imposed by the structure of a peptide in its alpha helical form, such pairs of acids can only form three specific acid pair types. In one acid pair type, designated EE (where E represents glutamic acid), no amino acid intervenes in the peptide backbone between the carboxylic acid side chains forming the acid pair. In another acid pair type, designated EXXE (where X is an amino acid other than glycine or proline), two amino acids intervene in the peptide backbone between the carboxylic acid side chains forming the acid pair. In the third acid pair type, designated EXXXE, three amino acids intervene in the peptide backbone between the carboxylic acid side chains forming the acid pair. FIG. 4b shows a two-dimensional depiction of such a double-hydrogen-bonded carboxylic acid pair structure in a peptide sequence where there are two amino acids intervening between the paired carboxylic acid side chains of two glutamic acids (EXXE acid pair type). For the demanding case of peptide entry into membranes of cells in acidic areas of tumors, the intervening amino acids must be lipophilic. Thus, the acid pairs suitable for transporter peptides of the instant invention are: EE, ELLE, and ELLLE.

It has been found that in order to afford adequate aqueous solubility at the pH in normal tissues, but transporter activity at pH values present in acidic areas of tumors, the transporter peptide should contain at least three acid pairs, with the upper limit on number of acid pairs being dictated by cost and other practical considerations. As noted above, the two carboxylic acids of an acid pair should be separated by zero, two, or three intervening lipophilic amino acids.

5. Axial Distribution of Acid Pairs in Transporter Peptide

Applicant has found that most peptides containing three or more carboxylic acid pairs and an amino acid composition of greater than 50% lipophilic amino acids will rapidly aggregate in acidic aqueous solution. Such rapid aggregation appears to strongly compete with entry into cell membranes, rendering such rapidly-aggregating peptides poorly effective for transporting into cells in acidic areas of tumors. However, this problem of rapid aggregation can be considerably reduced by utilizing amino acid sequences which provide a fairly balanced distribution of acid pairs about the helical axis of the transporter peptide in its alpha helical conformation.

In a peptide alpha helix each consecutive amino acid side chain is rotated 100 degrees about the helical axis relative to the previous amino acid side chain. Thus, 3.6 amino acids give one full turn of the peptide backbone around its helical axis. To facilitate design of transporter peptides, amino acid side chain positions can be plotted on a spiral graph wherein each successive numbered amino acid side chain position is rotated 100 degrees about the helical axis relative to the previous amino acid side chain, and each successive amino acid side chain is plotted a standard increment further out from the helical axis relative to the previous side chain in the peptide. Using such plots, the two carboxylic acids of each acid pair are then connected by a bold line to allow visualization of the distribution of the acid pairs of a transporter peptide in two dimensions, both with respect to their distribution around the helical axis and with respect to their distribution along the length of the peptide helix.

FIG. 5a shows both the sequence and the axial distribution plot of acid pairs for two peptide sequences wherein the acid pairs are positioned largely on just one side of the peptide's helical axis. Such peptides suffer from rapid aggregation and poor embedder activity. FIG. 5b shows the sequence and the axial distribution plot of acid pairs for two preferred transporter peptide sequences wherein the acid pairs are more evenly distributed about the helical axis. These latter transporter peptides are slower to aggregate under acidic conditions and thus are considerably more effective for transporting into cells in acidic areas of tumors.

When one considers only transporter peptides which have a high enough pT value to transition to their lipophilic form in acidic areas of tumors, applicant's recent molecular modeling studies and octanol/buffer partitioning experiments with test peptides, carried out in support of the instant invention, suggest that in order to avoid undue aggregation of such high-pT transporter peptides under acidic conditions, for most cases the axial center point of an acid pair should be rotated relative to the axial center point of the next acid pair (designated the "axial rotation between pairs") by a defined number of degrees selected from the group consisting of 450, 500, 550, 600 and 650, and the average of all axial rotations between pairs for a given transporter peptide should be in the range of about 500 to about 600 degrees. These five defined values for axial rotations between pairs correspond to 1.25, 1.39, 1.53, 1.67, and 1.81 helical turns, respectively, between the axial center points of consecutive acid pairs.

While the above rules hold for most cases, different axial rotation values should be used when EE type acid pairs are mixed with ELLE or ELLLE type acid pairs in a given transporter peptide. This is because the EE acid pair doesn't span from one helical turn of the peptide to another, while the ELLE and ELLLE acid pairs do. Thus, for cases where an EE acid pair is adjacent to an ELLE acid pair in the peptide, the axial rotation between those adjacent pairs should be 700 degrees, and where an EE acid pair is adjacent to an ELLLE acid pair the axial rotation between those adjacent pairs should be 750 degrees. FIG. 10 shows both the sequence and the axial distribution plot of acid pairs for representative transporter sequences with such mixed acid pair types.

While the above rules generally apply for core transporter peptide sequences suitable for use in acidic areas of tumors, recent experimental results with mammalian cells, carried out in support of the instant invention, suggest that when the average of the axial rotations between pairs in a transporter peptide is no more than 500 degrees, then the pE value is such that transporter activity will likely be limited to only the most-acidic areas of a tumor furthest from capillaries as illustrated in Comparative FIG. 2a labeled prior art. Likewise, when the core transporter peptide sequence contains 40% or more acid side chains, the pE value for said transporter peptide is also such that transporter activity will likely be limited to only the most acidic areas of tumors. In this context, it should be noted that 500 degrees is the highest value for the average of axial rotations between acid pairs in any of the prior art peptides covered in U.S. Pat. No. 6,030,941. Further, all of the core transporter peptide sequences covered in 941 contain 40% or more acid side chains—in particular, the peptides which contain the repeating amino acid sequences selected from [LELLE]n and [ELLLE]n.

Therefore, in order to achieve the desired goal of transporter activity in a broader range of acidic regions of tumors as illustrated in FIG. 2, one should use improved transporter peptide sequences of the instant invention. These peptides contain, but are not limited to, axial rotations between acid pairs of greater than 500 degrees. As noted earlier, experiments with mammalian cells suggests that to achieve activity in a broad range of acidic areas in tumors, the average of all axial rotations between acid pairs for a given transporter peptide should be greater than 500 degrees. It should be noted that the improved transporter peptides may contain one or more axial rotations of 500 degrees, or even 450 degrees, but must also contain one or more axial rotations of greater than 500 degrees. Furthermore, the average of all axial rotations between acid pairs within a given transporter peptide should be greater than 500 degrees. Such sequences with mixed axial rotation values averaging greater than 500 degrees in a given peptide are illustrated in FIGS. 9 and 10.

A systematic method has been developed for selecting improved transporter peptide sequences of the instant invention. As a basis for this method, FIG. 6 illustrates the key structural features of acid pair type and values of axial rotations between acid pairs used in selecting prospective amino acid sequences for transporter peptides. Using these key features, Example 1 and FIG. 7 illustrate a simple graphical procedure for selecting suitable transporter sequences. FIG. 8 shows two sets of transporter sequences, where the acid pairs within a single transporter peptide are of a single acid pair type. Acid pairs in the first set are all separated by 550 degree rotations. Acid pairs in the second set are all separated by 600 degree rotations.

As noted previously, a mixture of acid pair types and a mixture of axial rotation values can be used in the same transporter peptide. FIG. 9 shows both the sequence and the axial distribution plot of acid pairs for representative improved transporter sequences with mixed rotation values. FIG. 10 shows both the sequence and axial distribution plot of acid pairs for transporter peptides containing mixed acid pair types which include EE pairs.

6. Preferred Amino Acid Sequence Motifs in Transporter Peptide

In experimental work carried out to support the instant invention, it has been found that peptides which include particular sequence motifs often give exceptionally good transporter properties. Those properties include: a particularly high pE value, a sharp transition between the ionic and non-ionic forms; and, a minimal propensity to aggregate under acidic conditions. Two particularly preferred 16-amino acid sequence motifs are: ELLLELELLLELELLLE and ELLELELLLELELLEL. The preferred transporter composition below contains a transporter peptide sequence which includes both of these preferred sequence motifs (the motifs, which overlap in the full peptide sequence, are shown positioned above and below the full transporter peptide sequence).

ELLLELELLLELELLLE (motif)

Cargo-LELLLELELLELELLLELELLELELLLELL
(—NH—CH2—CH(CH3)$_2$)

ELLELELLLELELLEL (motif)

Each of these preferred sequence motifs contains less than 40% E (specifically: 37.5% E) and has an axial rotation between acid pairs which is greater than 500 degrees (specifically: 550 degrees), and so both sequence motifs satisfy the key criteria for improved transporter peptide sequences of the instant invention. It is noteworthy that a comprehensive search of the GenBank peptide and protein database (http://www.ncbi.nih.gov/protein) showed that neither of these preferred 16 amino acid sequence motifs are present in any know peptide or protein sequence deposited in that database (based on a search of all 787,608,532 amino acid letters of sequences deposited in this database as of 10 Feb. 2005).

7. Entry End of Transporter Peptide

It has been found that for a transporter peptide to readily enter a cell at a pH as high as that found in acidic areas of tumors, which is generally about pH 6.0 to about 7.0, it is necessary to make that terminus of the transporter peptide which is to first enter the membrane (designated the "entry end") fairly lipophilic. This includes rendering that terminus predominantly non-ionic at the pH in the acidic area of the tumor. In this regard, it has been found that relatively simple structural modifications to the terminus of a transporter peptide can substantially enhance its entry into cell membranes at pH values present in acidic areas of tumors. Adequate lipophilicity of the entry end can be achieved in a number of ways, such as described below.

When the C-terminus is to be the entry end, the normal C-terminal alpha carboxylic acid moiety typical of natural peptides and proteins can be replaced with a carboxylic acid side chain having a structure effective for forming a double-hydrogen-bonded acid pair structure with a nearby glutamic acid side chain, as illustrated in FIG. 11a. FIG. 11a shows the C-terminal entry end of a 22 amino acid-long transporter peptide, wherein at acidic pH the carboxylic acid of a C-terminal beta-alanine forms an acid pair with a nearby glutamic acid side chain. A C-terminal gamma-amino butyric acid can also be used for this same purpose. Alternatively, the normal C-terminal alpha-carboxylic acid typical of natural peptides and proteins can be rendered non-ionic by converting it to a lipophilic amide, as shown in FIG. 11b. Still greater lipophilicity can be obtained by also incorporating up to about three lipophilic amino acids at the C-terminus. FIGS. 11c and 11d show structures having the same core transporter sequence, but with one and two leucines, respectively, added to the C-terminus, along with the terminal lipophilic amide described above. FIG. 11 also tabulates the relative effects these various C-terminal modifications have on the pH at which these transporter peptides enter cell membranes (designated the "pE value", which is defined as the pH at which half of the transporter peptides have entered into cell membranes in the binding assay described in Example 6).

When the N-terminus is to be the entry end, the normal N-terminal alpha amine moiety typical of natural peptides and proteins can be capped with a lipophilic group, such as the pivalyl moiety, as illustrated in FIG. 12a. Still greater lipophilicity can be obtained by also incorporating up to about three lipophilic amino acids at the N-terminus. FIG. 12 illustrates two preferred lipophilic structures when the entry end is the N-terminus. In FIG. 12b a novel acid side chain serves to form an acid pair with a nearby acid side chain of glutamic acid. Such structures are easily prepared using pivalic anhydride or 3,3-dimethyl glutaric anhydride, as described in Example 2.

8. Chirality of Amino Acids in Transporter Peptide

At least 90%, and preferably 100% of the amino acids of a given transporter peptide should have the same chirality so that the transporter peptide will exist largely in its alpha helical conformation. While transporter peptides having amino acids with L chirality (the chirality of nearly all natural amino acids) can be acceptable, transporter peptides with D amino acids, which are more expensive than L amino acids, provide the advantage of being stable to most proteases and peptidases in the body, thereby helping to assure that the transporter peptide won't become separated from its cargo. Such resistance to enzymatic cleavage can be desirable when the cargo is a toxic substance which, if separated from its transporter peptide, might enter and damage cells in normal tissues.

9. Summary of Preferred Properties of Transporter Peptide

To summarize the characteristics of improved transporter peptides of the instant invention:

i) the length should be at least about 16 amino acids, and preferably longer than 23 amino acids;

ii) the transporter peptide should contain at least 3, and preferably 5 or 6 acid pairs, where acid side chains of a pair are separated by zero, two, or three amino acids in the peptide backbone;

iii) each acid of the acid pairs, except for the acid closest to the entry end, should be a side chain carboxyl moiety of glutamic acid;

iv) the acid side chain closest to the entry end should be a side chain carboxyl moiety of glutamic acid or another carboxyl-containing side chain effective to form an acid pair with a nearby glutamic acid side chain;

v) less than 40% of the amino acids in the core peptide sequence should be glutamic acids;

vi) at least 90%, and preferably 100% of the non-acidic amino acids should be lipophilic amino acids selected from the group consisting of: leucine, isoleucine, norleucine, and methionine;

vii) the axial rotation between the center point of one acid pair relative to the axial center point of the adjacent acid pair along the alpha-helical peptide backbone should be selected from the group consisting of 450, 500, 550, 600, and 650 degrees, with 550 degrees particularly preferred, except the axial rotation between an EE acid pair and an ELLE acid pair should be 700 degrees and the axial rotation between an EE acid pair and an ELLLE acid pair should be 750 degrees;

viii) the average of all axial rotations between pairs within a given transporter peptide should be greater than 500 degrees;

ix) the entry end of the transporter peptide should be modified to make it more lipophilic than in typical peptides and proteins, and it should be predominantly non-ionic at a pH within the acidic areas of a tumor; and, x) at least 90%, and preferably 100% of the amino acids of the transporter peptide should be of the same chirality.

B. Cargo Component of Transporter Composition

The key function of the cargo component, which must be sufficiently small and lipophilic that it can be pulled through the cell membrane by the transporter peptide, is to serve for detection or killing of cells into which the transporter composition has entered. The cargo component may contain one or more cargo moieties.

1. Cargo for Diagnostic Application (Diagnostic Moiety)

Desirable properties for a cargo which is to serve for diagnostic applications are:

a) it should not unduly reduce aqueous solubility, as is needed for effective distribution throughout the body;

b) it should not be so large that it cannot pass from capillaries into the interstitial space of tumors;

c) it should not be so large that it cannot be effectively cleared from normal tissues and excreted from the body;

d) it should not have a significant affinity for cell membranes at the extracellular pH in normal tissues; and, e) it should be readily detectable in an appropriate assay or with suitable equipment.

For such applications as research in tumor-bearing small animals, a cargo for diagnostic applications can be as simple as a fluorescent tag, such as a carboxyfluorescein or tetraethylrhodamine. Such fluorescent-tagged transporter compositions localized in acidic areas of tumors can be visualized in live mice by whole-body detection procedures known in the diagnostics art, or visualized more precisely by excising the tumor-bearing tissue and observing thin slices with a fluorescent microscope, as described in Example 8. Transporter compositions localized in tumors can also be extracted from the tissue and quantitated using a spectrofluorometer.

For non-destructive detection of transporter composition in tumors in larger animals, including humans, the cargo component of the transporter composition should generate a signal which is detectable from outside the body. Such signal-generating substances for this purpose are well known in the diagnostics art, and include such substances as radioisotopes (eg., technetium-99 and copper-64) and magnetic resonance contrast agents (eg., gadolinium). Incorporation of such signal-generating cargos into the transporter composition can be via attachment of any of a variety of known multi-dentate chelator moieties to the transporter peptide by a covalent link, followed by addition of the signal-generating radioisotope.

2. Cargo for Therapeutic Application (Therapeutic Moiety)

Desirable properties for a cargo which is to serve for therapeutic applications are:
  a) it should not unduly reduce aqueous solubility, as is needed for effective distribution throughout the body;
  b) it should not be so large that it cannot pass from capillaries into the interstitial space of tumors;
  c) it should not be so large that it cannot be effectively cleared from normal tissues and excreted from the body;
  d) it should not have a significant affinity for cell membranes at the extracellular pH in normal tissues; and,
  e) it should be effective for killing cells into which it has entered.

Therapeutic cargos include suitable radioisotopes, such as Cu64 and Re188, as well as elements which can be rendered radioactive in situ, such as non-radioactive boron that can be activated by a neutron beam. With proper selection of the radioisotope, the damage from decay products emanating from such cargos can be largely confined to cells in close proximity to the cargo, and so the damage is limited primarily to cells of the tumor.

Other therapeutic cargos can be selected from the hundreds of known natural toxins isolated from microorganisms, plants, and animals. Such toxins can be purchased from a variety of chemical and biological supply houses, such as Sigma-Aldrich, Saint Louis, Mo. A representative example of such a toxin with suitable properties for use as the cargo in a transporter composition is Cytochalasin B previously mentioned.

C. Linkage of Cargo to Transporter Peptide

Cargos of the invention are preferably linked to the transporter peptide by any of a wide variety of methods and through a wide variety of linkage types, FIGS. 15 and 16 illustrate several preferred linkages.

Figure 15A:
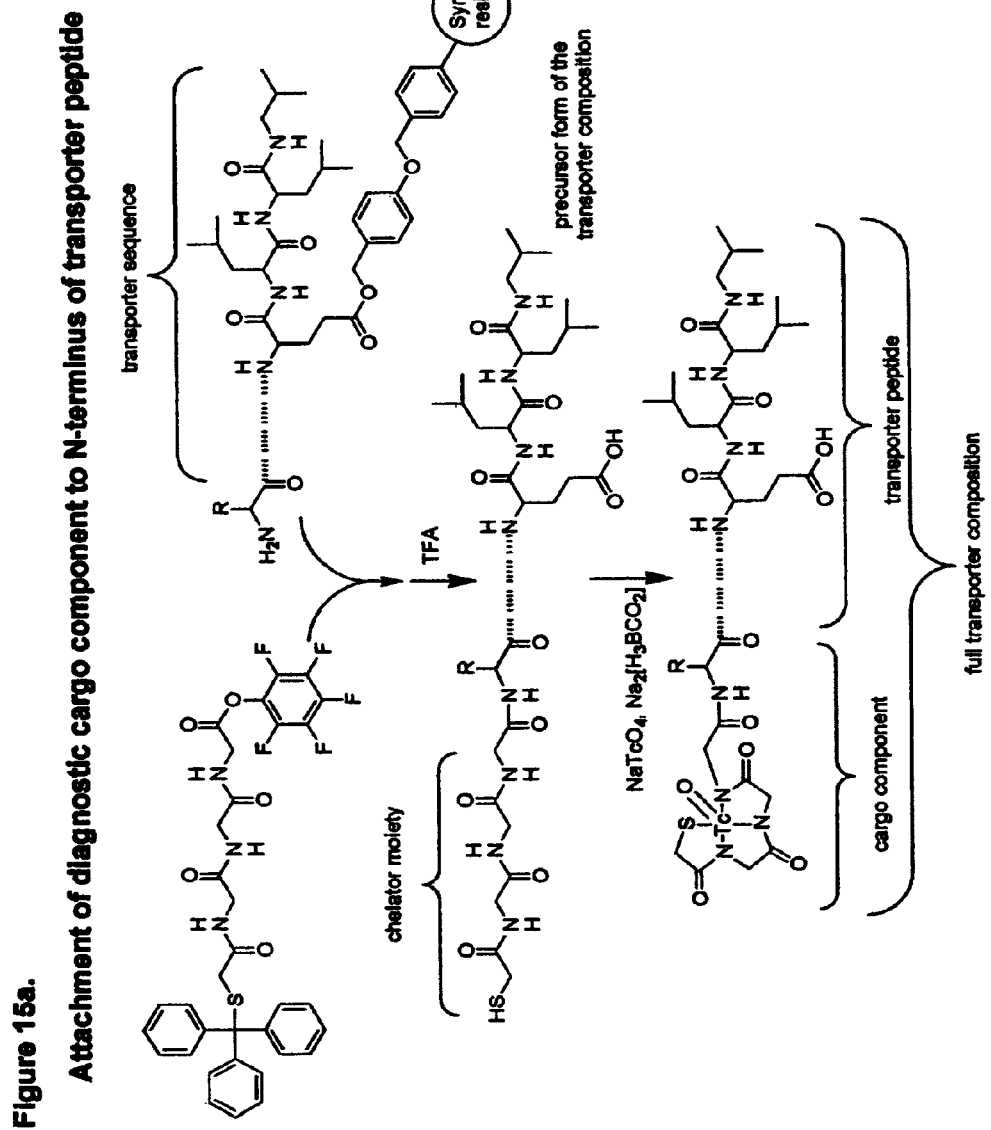
Figure 15B:
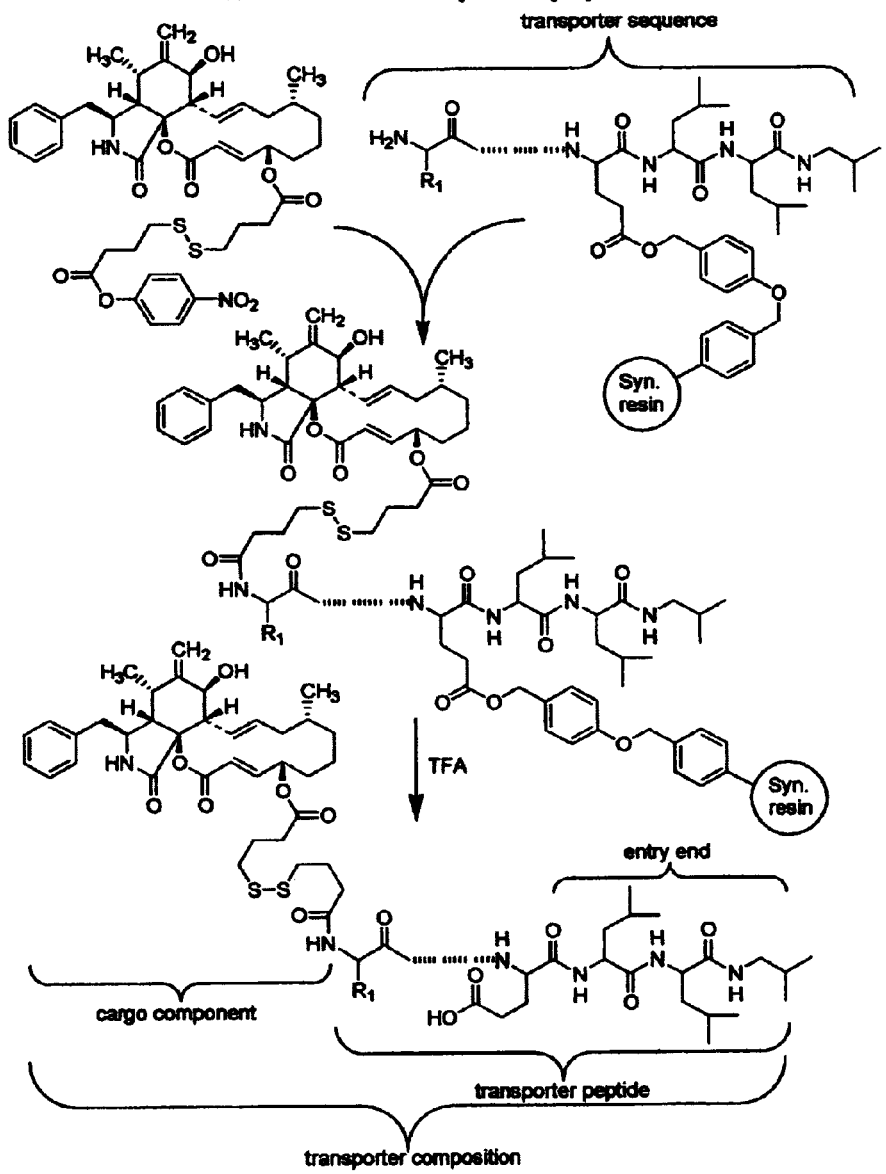
Figure 16A:
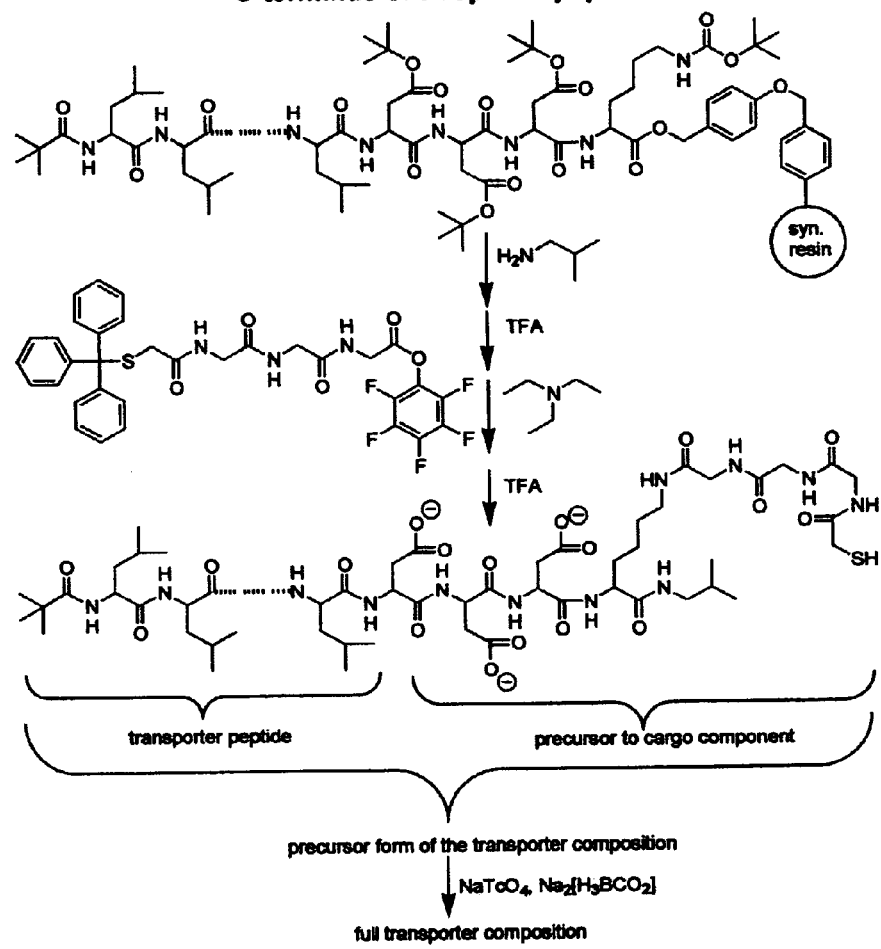
Figure 16B:
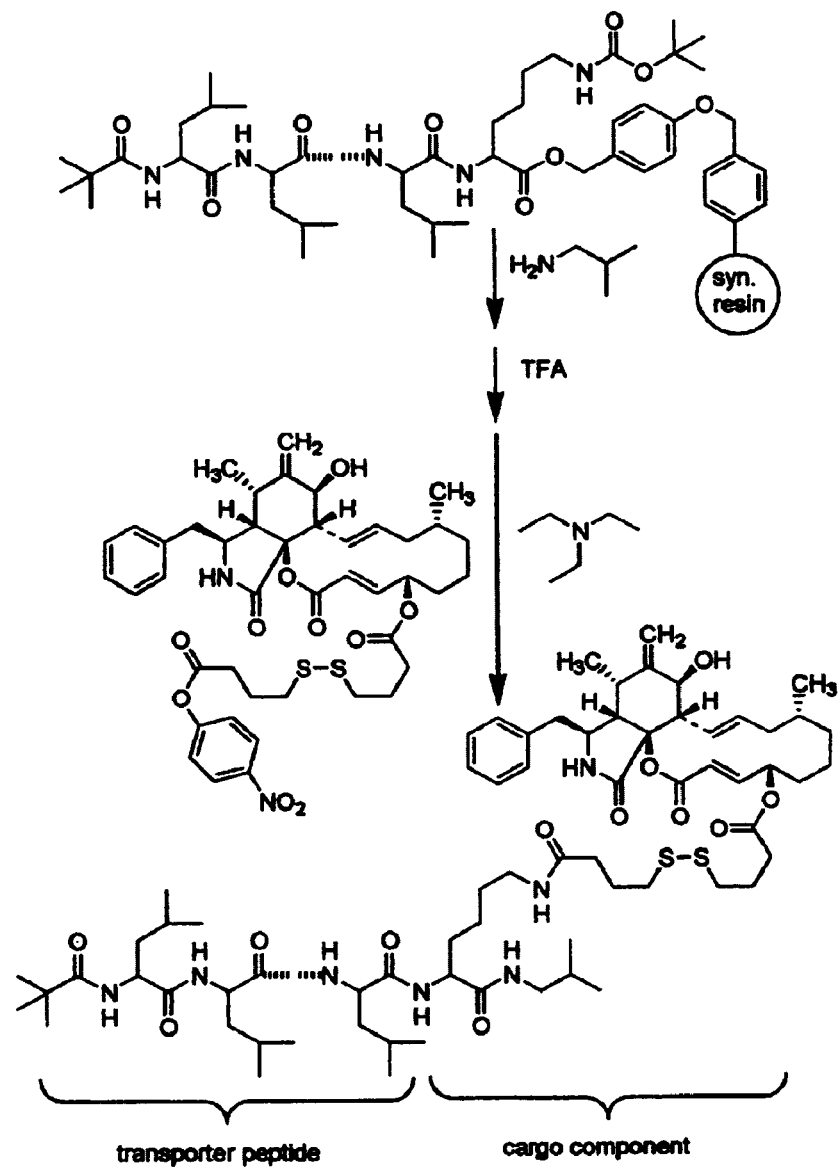

For many cargos it is particularly convenient to link the cargo to the N-terminal alpha amino moiety of the transporter peptide via an amide or carbamate link while that peptide is still on its synthesis resin and its side chain carboxyl moieties are still in the protected form, as illustrated in FIGS. 15a and 15b. Alternatively, cargos can be attached via a thioether linkage to either an N-terminal or to a C-terminal sulfhydral. Still another convenient way to attach a cargo is to add a lysine or cysteine amino acid at the terminus of the transporter peptide, and then, following cleavage of the peptide from its synthesis resin and cleavage of side chain protective groups, use the side chain amine or sulfhydral, respectively, for linking to the cargo, as illustrated in FIGS. 16a and 16b.

An alternative method for adding a cargo is to add several amino acids to the transporter peptide on the end distal to the entry end, such that the added amino acids are effective to strongly complex with a subsequently added cargo moiety. This strategy is illustrated for the case of a technetium cargo in FIG. 16c.

D. Transporter Composition with Multiple Cargos

It can be desirable to attach multiple cargos to a single transporter peptide, particularly for diagnostic applications. This can be accomplished by adding several lysines or several cysteines near the end of the peptide distal to the entry end, and then adding cargo moietes thereto.

E. Size of Transporter Composition

Since the cargo component of the transporter composition must be sufficiently small and lipophilic to be pulled through cell membranes by the transporter component, suitable cargos are generally less than about 2,000 Daltons. Furthermore, because of cost and ease of preparation considerations, there is seldom any reason to make transporter peptides larger than about 5,000 Daltons. Thus, the composite size of most transporter compositions is generally less than about 7,000 Daltons. Most substances of this size can readily pass through capillary walls anywhere in the body except the brain. Still further, substances of this size are generally rapidly filtered through the glomerulus into the urine in the kidney. Hence, while larger transporter compositions can be effective, on the basis of cost and function it is generally desirable to keep the size below about 7,000 or 8,000 Daltons.

F. Precursor Form of the Transporter Composition

Figure 16C:
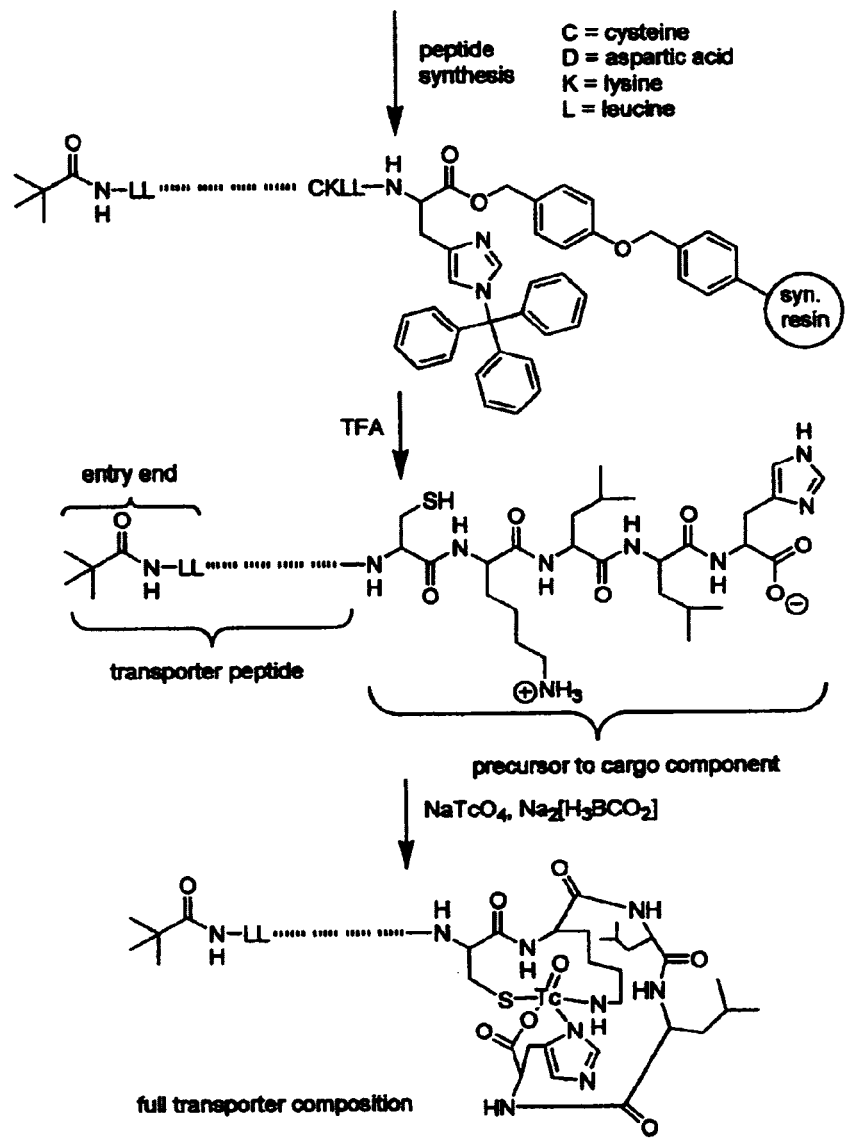

For many applications, a user of the transporter composition of the instant invention will obtain a precursor form of that transporter composition. Just before use, that precursor form of the transporter composition will be combined with a radioactive substance to generate the complete transporter composition, which will then be administered to the subject, such as an experimental animal or a patient. This formation of the completed transporter composition just prior to use is generally necessary when the radioactive substance which is to be a part of the cargo component has a short half life and so is only available just prior to its use. Such a precursor form of the transporter composition typically includes a chelator moiety effective to bind the radioactive substance. When said precursor form is contacted with said radioactive substance, the full transporter composition is formed. For example, in current practice well known in the nuclear medicine art, just before use technetium 99 is collected from a column of molybdenum, and then, after brief chemical processing, the technetium is quickly reacted with a suitable chelator moiety and the resulting product promptly administered to the subject. For the case of the instant invention, said suitable chelator moiety is the precursor form of the transporter composition. FIGS. 15a, 16a, and 16c illustrate, as the final step in synthesis of a transporter composition, such a conversion of a precursor form of the transporter composition to a a full transporter composition.

G. Representative Transporter Compositions

FIG. 13 shows three representative transporter compositions, showing amino acid sequence, entry end, and a cargo component.

H. Summary of Key Features of Improved Transporter Compositions

The following is a summary of the key features of an improved transporter composition. Specifically, a transporter composition comprises:

(a) a transporter peptide which is poly-anionic at pH 7.2 and above, and that converts to a lipophilic form effective to transport into cells at a pH below 7.2 that is present in acidic areas of a tumor, said transporter peptide containing
  (i) a peptide sequence ranging in length from about 16 to about 50 amino acids,
  (ii) wherein said peptide sequence contains at least three acid pairs, where said acid pairs except for the acid pair closest to the entry end are selected from the group consisting of EE, ELLE, and ELLLE,
  (iii) each acid of the acid pairs of said peptide sequence except for the acid closest to the entry end is a side chain carboxyl of glutamic acid,
  (iv) the acid closest to the entry end is selected from the group consisting of a side chain carboxyl of glutamic acid and another carboxyl-containing side chain effective to form an acid pair with a nearby glutamic acid side chain,
  (v) the number of acid side chains in the core transporter peptide sequence of said peptide sequence is less than 40% of the total side chains in the core transporter peptide sequence,
  (vi) in said peptide sequence the axial center point of one acid pair relative to the axial center point of the adjacent acid pair along the alpha-helical peptide backbone is rotated by a number of degrees selected from the group consisting of 450, 500, 550, 600, and 650 degrees, except for the rotation between an EE acid pair and an ELLE acid pair which is 700 degrees, and the rotation between an EE acid pair and an ELLLE acid pair which is 750 degrees,
  (vii) the average of the axial rotations between acid pairs in said peptide sequence is greater than 500 degrees,
  (viii) at least 90% of the non-acid side chain amino acids of said peptide sequence are lipophilic amino acids selected from the group consisting of leucine, isoleucine, norleucine and methionine,
  (ix) the entry end of said peptide sequence is predominantly non-ionic at a pH that is present in acidic areas of a tumor,
  (x) at least 90% of the amino acids of said peptide sequence are of the same chirality; and, (b) a cargo component which can be pulled across a cell membrane by the transporter peptide, and which contains at least one moiety selected from the group consisting of a diagnostic moiety and a therapeutic moiety.

II. Preparation of Representative Transporter Compositions

Methods for preparing peptides, including the transporter peptides of the instant invention, are well known in the art, and highly refined peptide assembly methods are widely described in the scientific literature, as well as in commercial sources such as the Nova Biochem Handbook and Catalog (Nova Biochem is an affiliate of Merck, KGaA, Darmstadt, Germany). In addition, a number of commercial entities will prepare specified custom-sequence peptides on request at reasonable prices.

In addition to the above generic methods for preparing peptides, Example 2 describes specific methods used for preparing representative transporter peptides of the instant invention, where the transporter peptides have preferred entry ends and have suitable sites for adding a variety of different cargo components. For simplicity, the peptide syntheses described herein used standard FMOC (fluorenyl methoxy carbonyl) peptide synthesis methods, but t-BOC (t-Butoxycarbonyl) syntheses or block assembly methods can also be used.

A. Transporter Composition with a C-Terminal Entry End

Example 2a describes two alternative methods for generating C-terminal entry ends. One method entails preparation of the peptide wherein the alpha-carboxyl of the C-terminal amino acid is linked to the synthesis resin via an ester linkage. After peptide assembly, the peptide is then cleaved from the synthesis resin using a suitable lipophilic primary amine. This generates a lipophilic amide on the entry end, as illustrated in FIGS. 11*b*, 11*c*, and 11*d*. An alternative method entails adding a pre-formed entry end to a Wang-type synthesis resin via an ester link to the gamma carboxyl of a glutamic acid, as illustrated in FIG. 14. The peptide is then cleaved from the resin by the standard TFA (trifluoroacetic acid) procedure. In both of these methods the N-terminal end is reserved for attachment of the cargo component containing one or more cargos. FIG. 15*a* illustrates on-resin N-terminal attachment of a representative cargo component for diagnostic application, and FIG. 15*b* illustrates how to attach a representative cargo component for therapeutic application.

B. Transporter Composition with an N-Terminal Entry End

Example 2b describes methods for generating two preferred N-terminal entry ends, as shown in FIG. 12, as well as incorporation of moieties near the C-terminus suitable for subsequent attachment of one or more cargo components. Methods by which one can attach cargos near the C-terminus are illustrated in FIGS. 16*a* and 16*b*.

III. Assessment of Properties of Transporter Composition

It is recommended that in order to develop an optimal transporter composition containing a selected cargo it is prudent to first prepare a variety of prospective transporter peptides, and then employ a series of increasingly complex assays to progressively narrow these down to one or a few which are best for a particular application. First testing a variety of prospective transporter peptides in simple, fast, and quantitative assays allows one to efficiently select the most promising amino acid sequences and entry ends for the transporter peptide. Then, after adding prospective cargo components, substantially fewer additional tests should be required to achieve effectiveness in vivo.

A. Partitioning and Aggregation Studies of Transporter Peptide

It is recommended that initial studies on prospective transporter peptides, typically labeled on their non-entry end with a suitable fluor such as carboxyfluorescein, should generally entail partitioning between n-octanol (which emulates the lipophilic interior of cell membranes) and a range of suitable buffers (emulating the extracellular medium within tumors and normal tissues), as described in Example 5a. This allows one to easily and quantitatively compare various transporter peptides with respect to the pH at which each converts from its anionic polar form to its non-ionic lipophilic form (the mid-point of this transition is referred to as the pH of transition, or pT value). It also allows one to easily compare the various transporter peptides with regard to how sharp the transition is between their anionic and lipophilic forms.

It is also desirable to compare the tendency of the different transporter peptides to aggregate as a function of pH. A suitable assay to assess aggregation as a function of pH is described in Example 5b.

B. Binding Studies with Red Cell Ghosts

In the course of applicant's earlier development of peptides designed to transport substances from a low-pH environment across a lipid layer to a higher-pH aqueous compartment, comprising the prior art transporter peptides described in U.S. Pat. No. 6,030,941, it was assumed that the pH at which the peptide converted from its anionic form to its lipophilic form in octanol/buffer partitioning assays provided a good estimate of the pH at which that peptide would enter a cell membrane. However, in the course of subsequent, more extensive studies in support of the instant invention, applicant has discovered that the pH value at which transporter components convert between their anionic form and their lipophilic form in octanol/buffer partitioning studies (the pT value) is significantly higher, on the order of about 0.5 to 1.0 pH unit, than the pH at which the transporter peptides will enter into a mammalian cell membrane (designated the "pE value"). The discrepancy between the pT value from a partitioning study and the pE value from a membrane entry study is probably because in a partitioning study when the peptide has lost some of its ionic charges its entry into the octanol phase can begin, and once begun, the further conversion of the partially-ionic peptide to its non-ionic lipophilic form is favored by the lipophilicity of the octanol phase it is entering.

In contrast, in order to begin entry into a cell membrane, it is probable that at least the entry end of the peptide must lose all of its multiple anionic charges before it can closely approach the anionic cell surface into which it is to initiate entry. Thus, pT values obtained from partitioning studies are primarily useful only for determining the relative order of the transporter peptides with respect to the pH at which they will transition between hydrophilic and lipophilic forms, as well as the sharpness of that transition. However, binding assays utilizing actual mammalian cell membranes to obtain pE values, such as is described in Example 6, are generally essential for selecting an optimal transporter peptide for a given application.

It should be noted that besides pH, it has recently been discovered that temperature also has a substantial impact on the ability of a transporter peptide to enter cells. Therefore, membrane binding studies and cell entry studies should not be carried out at room temperature, but instead should be carried out at the temperature at which the developed product will be used. This is 37 degrees C. when the transporter composition is to be used in humans.

Example 6 details a simple method to determine the pH at which a given transporter component will enter a representative cell membrane (the pE value). This red cell ghost assay is fast, easy, and gives precise quantitative results which appear to correlate well with results from similar studies in cultured cells. Preliminary results from in vivo studies also suggest that the pE values determined with red blood cell ghosts are predictive of transporter activity in tumors in live animals.

C. Cell Entry Studies with Cultured Cells

It is desirable to test both prospective transporter peptides and prospective full transporter compositions with cultured cells before moving to the more complex in vivo testing phase. It is recommended that the prospective transporter peptides containing just a fluorescent moiety for the cargo be tested first for entry into cultured cells, in order to narrow the selection to just a few of the more promising structures. Only then should full transporter compositions be prepared and tested in cultured cells.

Because even within a given tumor there is considerable heterogeneity in the permeability of the capillaries, the interstitial space in some regions of a tumor can contain considerable serum protein, while the interstitial space in other regions of the tumor may be relatively free of serum proteins. Since different transporter peptides appear to have differing affinities for serum proteins, particularly when the transporter peptides are in their non-ionic lipophilic form, it is prudent to compare entry into cultured cells by prospective transporter peptides both in culture medium free of serum, and in culture medium containing about 5% to 10% of serum.

As described in Example 7, it is recommended that the initial transporter studies with cultured cells entail preparing fluorescein-tagged transporter peptides, each in a series of culture media buffered at varying pH values ranging from about pH 6.0 (to emulate the most acidic regions of tumors) through 7.2 (to emulate the lowest pH typically found in normal tissues). The cultured cells, typically Hela, are then exposed to each transporter-containing medium for about 1 to 2 hours at 37 degrees C., washed with medium of the same pH but free of transporter component, and then the cells viewed under a fluorescent microscope to assess the amount and disposition of the fluorescent tag associated with the cells.

After treatment with transporter peptide, the living cells, without fixation, should preferably be viewed with an inverted microscope. This allows one to distinguish between fluorescence which is only on the cell surface and which gives a halo appearance, and fluorescence which is within the cytosol/nuclear compartment and which is most dense where the cell is thickest. If the fluorescence from the transporter peptide is only surface-bound it can be because the transporter peptide is too short (such as less than about 24 amino acids in length) or that the cells were exposed to a medium which was not sufficiently acidic to effect conversion of that particular transporter peptide to its lipophilic form. Once microscopic inspection indicates that cytosolic entry is achieved, a quantitative measure of entry can be made by dissolving the cells in aqueous 1% sodium dodecylsulfate buffered to pH 9, and the fluorescein moiety quantitated in a spectrofluorometer.

After a number of transporter peptides effective to enter cells at the desired pH (preferably about 6.5 to 6.9) have been identified in the above assay, where feasible, the next step is to prepare the full transporter composition and test it in cultured cells. This is most easily done when the cargo is a toxin which is effective to kill cells in which it has entered, such as Cytochalasin B. With such cargos the effect one looks for is simply killing of the treated cells. If such killing is not achieved, the problem may be that the transporter peptide was too short and/or the cargo was too large or too polar to be pulled through the cell membrane by the transporter component. Since it is crucial that intracellularly-acting toxin cargos be transported into the cytosol, if cell tests indicate that this is not achieved, then one should pick a different cargo or identify a more effective transporter peptide before proceeding to animal studies.

D. Studies in Tumor-Bearing Animals

The principal applications of the transporter compositions of the instant invention are for detection and treatment of tumors in animals, and particularly in humans. Accordingly, it is desirable that the prospective transporter compositions be thoroughly tested in vivo in animals whose physiology closely resembles that of humans in regard to body temperature; interstitial pH in normal tissues; the presence of acidic areas in tumors larger than microscopic size; and, blood clearance mechanisms. Mice satisfy these criteria and further constitute a well-studied model organism often used for tumor studies. It is recommended that the one or a few prospective transporter peptides which excelled in the in vitro and cell culture studies described above next be tested in mice, as described in Example 8.

For initial in vivo testing it is recommended that one first test prospective transporter peptides by injecting each fluorescent-tagged transporter peptide into at least two sets of tumor-bearing mice. After a suitable period of time, typically about 1 to 24 hours to allow washout from normal tissues, one set of mice are then used to assess the distribution of the transporter peptide throughout the organism. This entails removing the test tumor and major organs of the mouse, including liver, kidneys, lung, heart, and the like. After extracting the fluorescent-tagged transporter peptide from those tissues, the extracted fluor is quantitated on a spectrofluorometer. Generally a desirable transporter peptide is one which gives maximal labeling of the tumor, with little or no labeling of other tissues. The other set of mice are then used to assess the detailed spatial distribution of the transporter peptide within the tumors. This procedure entails removing each test tumor, freezing it, taking thin slices of the tumor in a cryostat, and finally viewing the tissue slices under a fluorescent microscope.

The design of subsequent in vivo tests of a full transporter composition will necessarily be dependent on the selected cargo. For instance, if the cargo is a chelated technetium-99 radioisotope, as discussed hereafter in Section VI.A., the final distribution of transporter composition in the animal can be determined in situ by standard scintography. Alternatively, if the cargo is a Cytochalasin B moiety, as discussed in Section VI.B., designed to kill cells into which the transporter composition has entered, then it may be desirable to initially generate tumors in the mice by inoculating the mice with transgenic tumor cells expressing luciferase. After tumors have formed, the mice are treated both with the transporter composition to effect destruction of the quiescent tumor cells, and with standard radiation or chemotherapy to effect destruction of the fast-dividing cancer cells. Regression of the tumors is then followed by periodic injection of an ester of luciferin into the mice and monitoring the living mouse for emitted light, which will be emitted by any residual live cancer cells.

IV. Formulation and Administration of Transporter Composition

For use in vivo it is generally desirable that the transporter composition be dissolved in an aqueous isotonic solution. Since the transporter peptides are largely insoluble in aqueous solution when the carboxyl side chains are in their free acid form, a base should be used to neutralize the acid moieties. It has been found that the sodium salt of transporter compositions generally have good aqueous solubility, while salts with organic amines, such as triethylamine, can have poor aqueous solubility. If sodium chloride (NaCl) is used to make the transporter solution isotonic the transporter composition may have inadequate aqueous solubility in the case of some of the more lipophilic transporter types. Therefore, instead of using NaCl, it is recommended that a suitable non-reducing carbohydrate, such as mannitol, be used to make the solution isotonic. Typically this is done by adding mannitol to a final concentration of about 0.3 Molar.

A representative method for formulating a transporter composition is as follows: Weigh out 20 microMoles of transporter composition in its free acid form (typically about 70 to 100 milligrams). Add 546 milligrams of mannitol, 9.5 milliLiters of water, and 0.1 milliLiter of 1 Molar aqueous sodium hydroxide (NaOH). Using a pH meter, while rapidly stirring slowly add more 1 M aqueous NaOH to effect complete dissolution of the transporter composition and raise the pH to about 8.0. This typically requires about an additional 0.1 ml of NaOH solution. Generally the transporter peptide of the transporter composition is stable to sterilizing temperatures (about 120 degrees C. for 30 minutes) and so if the cargo component is also stable to these temperatures, the transporter composition solution can be heat sterilized before use. If the cargo component is not sufficiently stable for heat sterilization, the solution can be filter sterilized by passing the solution through a sterile 0.2 micron filter before use.

For long term storage and for shipping it is often desirable to prepare an isotonic near-neutral solution of transporter composition, as above. This is frozen, then freeze-dried, capped, and heat sterilized at, for example, 120 degrees C. for 30 minutes. To use the preparation, simply add an appropriate volume of sterile water and shake to dissolve.

To assure efficient delivery into the vascular compartment of an animal, and particularly a human, and thence distribution throughout the body and into any tumors which are present, it is recommended that the transporter composition be administered by intravenous injection. While the 2 milliMolar transporter solution described above is suitable for most testing purposes, it should be appreciated that suitable concentrations of transporter composition for diagnostic and therapeutic applications are largely dependent on the identity of the cargo, and so should be empirically determined for each transporter composition.

V. Enhancement of Activity of Transporter Composition in Vivo

A. Use of Two or More Transporter Compositions Having Different pE Values

For tumors with acidic areas having a fairly broad range of pH values there is the potential that transporter compositions with too high of a pH of entry may aggregate or be largely bound to proteins or cell surfaces before reaching the lowest pH areas of the tumor most distant from capillaries. Alternatively, transporter compositions with too low of a pH of entry may fail to enter many cells in areas of higher pH closer to capillaries in the tumor. One strategy for dealing with a wide pH range within a tumor is to use a combination of at least two transporter compositions, one whose transporter peptide has a higher pH of entry and so is maximally effective in regions of the tumor which have a higher pH, and another whose transporter peptide has a lower pH of entry and so is maximally effective in regions of the tumor which have a lower pH. The rationale for using such a combination of transporters is that the composition with the higher pH of entry will be effective for entering cells of tumors in areas of higher pH close to capillaries, but may never reach areas of lower pH further from capillaries. Conversely, the composition with the lower pH of entry may be relatively ineffective in areas of higher pH close to capillaries, but will not aggregate or become bound to proteins or membranes in such regions and so can diffuse into and be fully effective when they reach areas of lower pH farther from capillaries.

B. Use of Substance to Selectively Further Reduce pH in Acidic Areas of Tumor

It has long been known that introduction of a rapidly-metabolized sugar, such as glucose, into tumor-bearing mammals acts to reduce the pH in the interstitial space in hypoxic areas of the tumors for about 1 to 2 hours, while having little or no effect on the pH of the interstitial space in normal tissues (Naeslund & Swenson (1953) Acta Obstet. Gynecol. Scand. 32, 359–367; Kozin, Shkarin, & Gerweck (2001) Cancer Research 61, 4740–4743; Prescott, Charles, Poulson, Page, Thrall, Vujaskovic, & Dewhirst (2000) Clinical Cancer Research 6, 2501–2505).

The pH in acidic areas of tumors can also be further reduced by treating with such agents as the mitochondrial inhibitor, meta-iodobenzylguanidine, again without undue effect on the pH in normal tissues (Kuin, Smets, Volk, Paans, Adams, Atema, Jahde, Maas, Rajewsky, & Visser (1994) Cancer Research 54, 3785–3792; Jahde, Volk, Atema, Smets, Glusenkamp, Rajewsky (1992) Cancer Research 52, 6209–6215).

Such substances, used alone or in combination, can improve both the diagnostic and the therapeutic utility of transporter compositions by increasing the proportion of cells of a tumor into which a transporter composition will enter. Alternatively, such induced temporary reductions in the pH within tumors can allow use of transporters with lower pE values, thereby even further improving the ability of the transporter composition to discriminate between tumor and normal tissues.

It is noteworthy that substances effective for further reducing the pH in acidic areas of tumors, such as glucose, can also be used to render prior art transporter peptides, covered by claims in the U.S. Pat. No. 6,030,941, effective in a somewhat wider range of acidic areas of tumors than would otherwise be the case. Thus, the prior art transporter peptides can be of greater value for detecting and treating tumors than is indicated in Comparative FIG. 2a (labeled prior art) if they are used in combination with pre-treatment of the patient with a substance effective for further reducing the pH in acidic areas of tumors. Accordingly, the instant invention also includes a method for detecting or treating tumors, where that method comprises first introducing into the patient a substance, such as glucose or glucose plus meta-iodobenzylguanidine, effective to temporarily further reduce the pH in acidic areas of tumors, and then treating the patient with one or more transporter compositions, each of which includes both: a) a transporter peptide that is poly-anionic at neutral pH, but converts to a non-ionic lipophilic form under acidic conditons achievable in tumors, and which is effective to transport a cargo from the acidic interstitial space of a tumor into the cytosol of a cell; and, b) a cargo component effective to detect or kill the cell which said composition has entered. Transporter peptides used in said method should have a composition wherein less than 45% of the amino acids in the core peptide sequence are glutamic acids, and wherein the average of all axial rotations between pairs within a given transporter peptide is at least 450 degrees.

C. Use of Substance to Minimize Re-Uptake of Transporter Composition in the Kidneys 1. Substance to Block Endocytotic Reabsorption by Proximal Tubules Peptides and proteins smaller than about 60,000 daltons are generally filtered from the blood into the urine in the glomerulus of the kidney. Peptides so filtered are subsequently reabsorbed from the urine by cells of the proximal tubule via receptor-mediated endocytosis. After endocytosis into proximal tubule cells, the peptides are subjected to peptidases and proteases of lysosomes which can lead to sequestering of degradation products within cells of the kidney and/or re-entry of degradation products back into the blood. Retention of components in the kidney may cause nephrotoxicity, and re-entry into the blood may compromise the goal of reducing background signal in normal tissues via excretion of non-tumor-bound transporter composition from the body. If such endocytotic reabsorption by proximal tubules proves to be a significant problem for a given transporter composition, it may be desirable to additionally treat the patient with a substance which is effective to reduce reabsorption of peptides by the proximal tubules, such as D-lysine, thereby speeding clearance of the transporter composition from the body. Use of D-lysine for reducing reabsorption of peptides in the kidney is described in: Bernard, Krenning, Breeman, Rolleman, Bakker, Visser, Macke, de Jong, Journal of Nuclear Medicine 38, 1929 (1997).

2. Substance to Make Urine Alkaline

Urine is often acidic. Transporter composition which has been filtered from the blood into the urine will convert in such acidic urine to its non-ionic lipophilic form, which can then directly transport across the plasma membrane of cells lining the glomerulus and proximal tubule of the kidney. When the cargo is a diagnostic moiety this re-entry into cells of the kidney can limit the ability to detect tumors anywhere near the kidney. When the cargo is a therapeutic moiety this re-entry into cells of the kidney can cause nephrotoxicity. To avoid problems caused by acidity of the urine, the urine can be temporarily rendered moderately alkaline by a number of methods known in the medical arts for acute treatment of acidosis. One widely used method which increases the pH in the urine is simply to feed the patient an appropriate dose of sodium bicarbonate by mouth. This would be done prior to, and possibly during treatment with the transporter composition. This simple measure can assure that the urine remains slightly basic during the time the excess transporter composition not incorporated into cells of tumors is being cleared from the body through the kidneys.

VI. Diagnostic and Therapeutic Applications of Transporter Composition

A. Diagnostic Application

Largely because of the great variability between tumors, routine detection of a wide range of tumor types at a sufficiently early stage that they can be successfully treated, preferably before they show symptoms, has long been an unmet goal of medicine. Much of the difficulty in routine early detection of tumors has been in finding and exploiting some property which is common to most or all tumors, and which can be effectively exploited for routine and affordable detection of very-early-stage tumors. While it has been known for over seventy years that tumors larger than microscopic size contain hypoxic areas wherein the interstitial pH is lower than in normal tissues, until applicant's instant discovery this common property of tumors had not been exploited for detecting tumors.

The transporter compositions having diagnostic cargos disclosed herein exploit this interstitial acidity in tumors to provide a new and novel means for detecting tumors. Coupled with modern imaging technologies, these transporter compositions offer the promise of routine detection of a wide range of tumor types. It is envisioned that suitable transporter compositions can be used routinely in annual physical exams for early detection of even very small tumors, allowing their treatment at much earlier stages of tumor development where cure rates are highest.

FIG. 17 shows two representative transporter compositions designed for detection of tumors containing acidic regions. The shorter of the two transporter peptides in these diagnostic compositions undergoes a transition to its lipophilic form at a pH about 0.2 pH unit lower than the corresponding transition of the longer peptide, and so when used together these two compositions may provide better tumor detection than either used alone. In these compositions the transporter peptide is linked to a precursor to the cargo component which contains a chelator moiety effective to strongly bind Technetium. Chelators of this structure are widely used for binding technetium. After formulation as described in Section IV herein, just before injection into a patient, freshly-prepared radioactive technetium is reduced in situ and the reduced form complexed with the chelator moiety of the precursor form of the transporter composition, as illustrated in FIG. 15a, thereby generating the full transporter composition ready for injection into the patient. Complexing with technetium is preferably carried out in a single step in a single vial using a commercially available kit, such as the Isolink Kit (available from Mallinckrodt, Philipsburg, N.J.).

The technetium-containing transporter composition is next injected into the patient. After a suitable period of time to allow for clearance of transporter composition from normal tissues, such as about 1 hour to 24 hours, the patient is scanned with a gamma scintillation camera (standard in modern Nuclear Medicine Departments) to show the position and size of any tumors which are present in that patient.

To increase diagnostic sensitivity and specificity, about 30 minutes before injecting the transporter composition the patient can be pre-treated with a substance, such as glucose or glucose plus meta-iodobenzylguanidine, to further temporarily reduce the pH within acidic areas of any tumors present in the patient.

To minimize endocytotic re-uptake of transporter composition from the urine in the proximal tubules of the kidney, the patient may be pretreated with a substance which is effective to reduce reabsorption of peptides by the proximal tubules, such as D-lysine.

To avoid acid-mediated re-uptake of transporter composition from the urine due to low-pH urine, the patient may be fed an appropriate dose of sodium bicarbonate by mouth prior to, and possibly during treatment with the transporter composition.

B. Therapeutic Application

While rapidly dividing tumor cells can be efficiently killed by conventional radiation and chemotherapy, the slow-dividing and non-dividing tumor cells in acidic areas of tumors are far more resistant to killing by such conventional therapies. While several therapies have been developed to exploit the hypoxia in tumors, to date there appear to be no reports of cancer therapeutics explicitly designed to exploit the acidity within tumors to effect selective killing of quiescent tumor cells while avoiding damage to cells in normal tissues.

The transporter compositions having therapeutic cargos disclosed herein are designed to exploit this interstitial acidity in tumors to provide a new and novel means for selectively killing the normally-treatment-resistant cells in acidic regions of tumors. Coupled with conventional cancer therapies effective for killing fast-dividing tumor cells, said transporter compositions offer the promise of more effective treatment and far fewer relapses for a wide range of tumor types.

FIG. 18 shows two representative transporter compositions designed to kill cells in acidic areas of tumors. As in the diagnostic set in FIG. 17, the shorter of the two transporter peptides in these compositions undergoes a transition to its lipophilic form at a pH about 0.2 pH unit lower that the corresponding transition of the longer transporter peptide, and so when used together these two compositions may provide better therapeutic effect than either used alone. The cargo of these transporter compositions, Cytochalasin, is a small lipophilic toxin which acts within the cell to inhibit actin polymerization. After formulation as described in Section IV, the transporter composition is injected into the patient. Preferably, said treatment with transporter composition is carried out in combination with a conventional cancer therapy to best assure destruction of both quiescent and fast-dividing cells of the tumor.

To increase the therapeutic efficacy, about 30 minutes before injecting the transporter composition the patient can be pre-treated with a substance, such as glucose or glucose plus meta-iodobenzylguanidine, which is effective to further temporarily reduce the pH within acidic areas of any tumors present in that patient.

To minimize endocytotic re-uptake of transporter composition from the urine in the proximal tubules of the kidney, the patient may be pretreated with a substance which is effective to reduce reabsorption of peptides by the proximal tubules, such as D-lysine.

To avoid acid-mediated re-uptake of transporter composition from the urine due to low-pH urine, the patient may be fed an appropriate dose of sodium bicarbonate by mouth prior to, and possibly during treatment with the transporter composition.

EXAMPLES

Example 1

Graphical Method for Identifying Amino Acid Sequences for Improved Transporter Peptide There are 10 to the 31st power (more than a billion times a billion times a trillion) possible amino acid sequences for a peptide just 24 amino acids long and composed of just the 20 standard amino acids used in nature. However, of this vast number of possible peptide sequences, only an infinitesimally tiny fraction, on the order of a few thousand, can effectively serve as a transporter peptide effective in the pH range present in acidic areas of tumors. Of these few thousand effective sequences, fewer still have a high enough pE to be effective in a majority of the acidic areas of tumors. These exceptional transporter sequences effective in a majority of the acidic areas of tumors constitute the improved transporter peptides of the instant invention. The following rules and procedures allow one to readily select such improved transporter peptide sequences from the vast sea of possible peptide sequences which would be ineffective as transporters in acidic areas of tumors, or, as is the case for prior art transporter peptides, would be effective in only the most acidic areas of a tumor comprising only a small fraction of the total acidic areas of a tumor. The rules are summarized below.

a) All carboxylic acid side chains of the transporter sequence should be glutamic acids, excepting the carboxylic acid closest to the entry end, which may be either a glutamic acid side chain or some other carboxyl-containing structure effective to form an acid pair with a nearby glutamic acid side chain, such as illustrated in FIGS. 11a and 12b.

b) Every carboxylic acid should have a carboxylic acid pairing partner capable of forming a doubly-hydrogen-bonded acid pair structure selected from the three types shown in FIG. 6a, excepting the acid closest to the entry end may have a different structure, but still effective to form an acid pair with a nearby glutamic acid side chain, such as illustrated in FIGS. 11a and 12b.

c) The acid side chain content in the core transporter peptide sequence should be less than 40% of the total side chains.

d) The axial rotation between center points of consecutive acid pairs should be selected from the group consisting of 450, 500, 550, 600, and 650 degrees, as illustrated in FIG. 6b, excepting the rotation between an EE acid pair and an ELLE acid pair should be 700 degrees, and the rotation between an EE acid pair and an ELLLE acid pair should be 750 degrees, as illustrated in FIG. 10.

e) The average of axial rotations between acid pairs in a given transporter peptide should be more than 500 degrees.

f) At least 90%, and preferably 100% of the amino acids which do not have carboxylic acid side chains should be lipophilic amino acids selected from the group consisting of: leucine, isoleucine, norleucine and methionine.

FIG. 7 illustrates a simple stepwise procedure to apply these rules for selection of improved transporter peptide sequences. This procedure entails the following steps:

First, mark out positions for at least 16 amino acids, but preferably positions for about 24 to about 33 amino acids.

Second, starting from one end, pencil in one of the three acid pair types and mark its center point.

Third, pencil in a second center point for the next acid pair, with the axial rotation value between these consecutive center points selected from the group consisting of 450, 500, 550, 600, and 650 degrees, as illustrated in FIGS. 8 and 9, or the axial rotation value selected from 700 and 750 degrees for the special cases illustrated in FIG. 10. It should be noted that moving from one amino acid position to the next corresponds to an axial rotation of 100 degrees.

Fourth, using that second center point, enter an appropriate second acid pair, again selected from the three types shown in FIG. 6a.

Continue to add acid pairs in this manner until the peptide sequence contains at least three, but preferably 4 to 6 acid pairs.

Next, fill the intervening amino acid positions with lipophilic amino acids, preferably leucines, as illustrated in FIGS. 7a(iii) and 7b(iii).

The prospective transporter peptide sequence generated above should then be assessed to assure that less than 40% of the side chains of the core transporter peptide sequence are acid side chains, and that the average of the axial rotations between acid pairs is more than 500 degrees.

After a transporter peptide sequence has been selected by the above steps, the next step is to pick which end of the peptide (C-terminal or N-terminal) is to be the entry end. Generally either end works equally well, but picking one over the other may significantly affect the required synthetic effort when subsequently adding particular cargo components. FIGS. 11 and 12 illustrate representative entry ends of both the C-terminal and the N-terminal types, and FIG. 14 shows one method for preparing a representative C-terminal entry end. These and closely related entry ends are relatively easy to prepare and suitable for most applications. More complicated end structures can also be used if it is desirable to make the entry end even more lipophilic. However, it should be appreciated that excessive lipophilicity of an entry end can lead to aggregation problems, which ultimately can reduce instead of increase transporter efficiency.

Example 2

Preparation of Representative Transporter Peptides

Transporter peptides used in experimental studies carried out in support of the instant invention have generally been synthesized on a Wang resin using an automated peptide synthesizer provided with fluorenylmethoxycarbonyl-protected/pentafluorophenyl ester-activated amino acids. The C-terminal amino acid of the peptide is typically linked to the synthesis resin via the acid-leavable ester linkage characteristic of the Wang type resin. Except where noted otherwise, deprotection and cleavage from the resin is with trifluoroacetic acid (TFA), plus triisopropylsilane/water to scavenge carbonium ions generated in the deprotection step. These methods are well known in the art and are detailed in the NovaBiochem Handbook and Catalog, 2000.

a) Transporter Peptides with C-terminal Entry Ends

C-terminal entry ends having one, two, or three C-terminal leucines, and capped with a terminal lipophilic amine, such as shown in FIGS. 11c and 11d, generally give effective entry into membranes.

One convenient way to generate such entry ends is to simply prepare the peptide sequence with the appropriate number of leucines at the C-terminus, and then cleave the peptide from the resin using neat isobutylamine. In this method, the completed peptide, still on the synthesis resin and with side chains still protected, is washed with dichloromethane and dried under vacuum. One gram of the dry resin/peptide preparation is then added to 20 ml of isobutylamine, the container capped tightly, and the preparation incubated at 50 degrees C. for 4 to 6 hours. About once each hour during the course of this incubation the container is inverted several times. The preparation is next filtered into a rotovap flask and the resin washed repeatedly with trifluoroethanol to wash the released peptide, now with a C-terminal isobutylamide, from the synthesis resin. The isobutylamine and trifluoroethanol are rotovaped off in a warm water bath. 100 ml of acetonitrile is added to the peptide residue and rotovaped off. The peptide residue is then treated with trifluoroacetic acid/triisopropylsilane/water in the conventional manner to deprotect the amino acid side chains. For typical peptides ether is used to wash the peptides after deprotection with TFA. However, it is recommended that such standard procedures not be followed, and instead the transporter peptides be washed with a 1:1 mixture of t-butylmethylether:hexane. This is because typically the transporter peptides of the instant invention are fairly soluble in ether and so considerable losses are incurred in the standard ether washing procedure.

For cargo components or precursor cargo components which are stable to the above processing conditions, said components can be linked to the N-terminal amine of the peptide while the peptide is still on the synthesis resin and its side chains still protected, as illustrated in FIGS. 15a and 15b. When the cargo component or precursor cargo component is added to the peptide while the peptide is still on its synthesis resin and side chains still protected, the resultant transporter compositions are typically suitable for experimental use without special purification. However, if the cargo components are not stable to the above conditions, the cargo component should be linked to the N-terminal amine, or to an N-terminal lysine side chain, or to an N-terminal cysteine side chain after the peptide has been fully deprotected. In such cases purification of the product is generally required.

Because of the high concentration of a fairly strong primary amine base at a fairly high temperature for a number of hours, the foregoing procedure for generating a lipophilic amide on the C-terminus may cause some racemization of the peptide (but not observed in our preliminary assays). To preclude such possible racemization, a lipophilic C-terminal amide can be introduced by the method illustrated in FIG. 14. While this alternate route entails greater synthetic effort up front, it has the merit of simpler processing of the final peptide product—generally requiring only the standard deprotection and cleavage from the resin with trifluoroacetic acid/triisopropylsilane/water. This later procedure also offers the advantage of allowing on-resin linking of the cargo component to the N-terminus of the peptide when that cargo component would be damaged by treatment with isobutylamine, but not with TFA, such as illustrated in FIGS. 15a and 15b.

After synthesis and processing, the mass of each transporter composition or precursor to the transporter composition is typically confirmed by disolving about 0.1 mg in 50 microliters of methanol, and then running a matrix assisted laser desorption ionization time of flight mass spectrum.

b) Transporter Peptides with N-terminal Entry Ends

N-terminal entry ends having one, two, or three N-terminal leucines and a pivalamide cap are prepared simply by synthesizing the appropriate peptide sequence, and then, after removing the terminal FMOC protective group, reacting the resin-bound/side chain-protected peptide with pivalic anhydride. After subsequent processing, this gives an entry end structure such as shown in FIG. 12a. Alternatively, N-Terminal entry ends having two or three leucines capped with 3,3-dimethyl glutaryl group, with its built in acid side chain, are prepared simply by synthesizing the appropriate peptide sequence, and then, after removing the terminal FMOC protecting group, reacting the resin-bound/side-chain-protected peptide with 3,3-dimethylglutaric anhydride. After subsequent processing this gives a structure such as illustrated in FIG. 12b.

For transporter peptides which contain an N-terminal entry end, it is typically necessary to provide a suitable handle at or near the C-terminus for attachment of the cargo component or precursor to the cargo component—though this requirement can be circumvented in such cases where the cargo component or a precursor to the cargo component is incorporated into the peptide sequence during peptide synthesis, as illustrated in FIG. 16c.

FIGS. 16a and 16b illustrate a preferred scheme for linking a cargo component to the side chain amine of a C-terminal lysine. A similar scheme can be used to link to the side chain sulfhydral of a C-terminal cysteine. For example, when the cargo component contains a chloroacetamide moiety, or acrylamide moiety such coupling will generate a thioether linkage. These and many other methods for linking cargo components to the transporter peptide are well known in the chemical art, such as described in the book: Bioconjugate Techniques (Hermanson, 1996).

Example 3

Attachment of Representative Cargo for Diagnostics Application

The MAG3 moiety (mercaptoacetic-glycine-glycine-glycine) is a very robust moiety which is widely used for covalently linking to biological structures and subsequently complexing with an added technetium 99. Because of its simplicity, ease of preparation, and ease of attachment to a transporter peptide of the instant invention, use of this moiety is preferred for generating a precursor form of the transporter composition, as illustrated in FIG. 15a. Just before use, that precursor form of the transporter composition is contacted with a suitable preparation of technetium 99 to generate the full transporter composition, and that composition is then injected into the subject for the purpose of detecting tumors in said subject.

Example 4

Attachment of Representative Cargo for Therapeutic Application

Many of the intracellular-acting toxins which might be suitable as cargos in transporter compositions of the instant invention are derived from natural sources (bacteria, plants, animals). As a consequence, many such toxins are most effective when they are unencumbered by a large attached group, such as the transporter peptide. Therefore, it is desirable to devise a linkage between the toxin and the transporter peptide which: a) will be stable in the extracellular medium; and, b) will be cleaved to regenerate the original toxin after the transporter compositon has entered the cell in an acidic area of a tumor.

FIGS. 15b and 16b show a novel linkage with just such desired properties. Applicant's preliminary experimental results suggest that when the bi-functional reagent, 4,4'-dithiodibutyric acid is used to join an alcohol of one substance to an amine of a second substance, that linkage is stable in extracellular media (oxidizing conditons). However, when substances joined by this novel linkage enter a cell (reducing conditions) those two substances are cleaved apart and the alcohol component appears to be regenerated in its original form. This cleavage process is most likely due to intracellular glutathione cleaving the disulfide bond of this novel linkage, and subsequent intramolecular attack of the liberated sulfhydral moiety on the proximal ester bond, which thereby regenerates the original alcohol component. Using such a novel linkage, the Cytochalasin B toxin should be transported to and then into cells in acidic areas of tumors by the attached transporter peptide, and then that toxin released into the cytosol of that cell in its fully active native form effective to kill the cell.

Example 5

Biophysical Studies of Transporter Peptide a) Partitioning Between n-Octanol and Aqueous Buffers Partitioning between octanol and aqueous buffer provides information on the pH at which a transporter peptide undergoes the transition between its poly-anionic form and its lipophilic form (the pH of transition, or pT value). For such studies one should prepare the transporter peptide with a fluorescein tag on the end which is distal to the entry end. A 1.0 milliMolar stock solution of this fluorescent-tagged transporter peptide is prepared comprising 1.0 microMole of such transporter peptide, in its free acid form, dissolved in 1 ml of dimethylformamide or isopropanol. These studies are carried out at room temperature.

Prepare the following buffer solutions:

0.1 M 2-(Morpholino)ethanesulfonic acid (MES) (pKa 6.1).

Using 5 M aqueous NaOH, adjust portions to:
   a) pH 5.8
   b) pH 6.0
   c) pH 6.2
   d) pH 6.4

0.1 M N-(2Acetoamido)-2-aminoethanesulfonic acid (ACES) (pKa 6.8).

Using 5 M aqueous NaOH, adjust portions to:
   e) pH 6.6
   f) pH 6.8
   g) pH 7.0

0.1 M 4-(2-Hydroxyethyl)piperazine-1-ethanesulfonic acid (HEPES) (pKa 7.5).

Using 5 M aqueous NaOH, adjust portions to:
   h) pH 7.2
   i) pH 7.4
   j) pH 7.6
   k) pH 7.8

To each of eleven 0.75 ml shell vials add:
   5 microLiters of transporter peptide solution
   300 microLiters of n-octanol
   300 microLiters of one of the above buffer solutions Cap, shake vigorously for 1 minute, then centrifuge to separate the phases.

To each of 22 shell vials add 0.85 ml of base solution (2% tetramethyl guanidine/98% isopropanol, v/v), and then add 150 microLiters of the upper octanol phase from each of the 11 test samples to 11 vials of base solution, mix and then measure the absorbance value of each at 496 nm. Next, carefully remove as much of the octanol upper phase as possible from each of the test samples and then add 150 microLiters of the lower aqueous buffer phase from each of the 11 test samples to 11 vials of base solution, mix and then measure the absorbance value of each at 496 nm. Plot the absorbance values for both the octanol phase and the buffer phase as a function of pH. The pH at which the two plots cross is the pH of transition, or pT value, for that transporter peptide.

b) Aggregation in Aqueous Buffers

Aggregation studies are carried out the same as above except without the octanol phase. In this case one plots as a function of pH only the absorbance of the buffer phase after centrifugation, and the pH at which the absorbance has dropped to half of the maximum value is taken as the pH of aggregation, or pA value. Typically, for a good transporter peptide the pA value is about 0.3 to 0.4 pH unit below the pT value.

Example 6

Binding Studies with Red Cell Ghosts

Red blood cell ghosts can be used to easily, rapidly, and quantitatively determine the pH at which a transporter component will enter into membranes of human cells (the pE value). To begin, place 10 ml of fresh human blood in a 50 ml centrifuge tube, add 40 ml of normal saline (0.15 M NaCl), cap, centrifuge down the red cells, and discard the supernatant. Resuspend the cell pellet in another 45 ml of normal saline and again centrifuge down the red cells and discard the supernatant. Repeat this wash process one more time. To the cell pellet rapidly add 45 ml of distilled water to release the hemoglobin from the red cells. Cap and centrifuge down the red cell ghosts (typically 10,000 rpm for 10 minutes). Carefully draw off the red supernatant and discard, leaving the pink pellet of red cell ghosts. Suspend the pellet of ghosts in 45 ml of normal saline/0.1% sodium azide, centrifuge down the ghosts, discard the supernatant, and resuspend the pellet in 3 ml of normal saline/0.1% sodium azide. This red cell ghost suspension should be kept on ice during the experiment, and may continue to be used for several days if stored at 4 degrees C.

Prepare 1 milliMolar stock solution of fluorescent-tagged transporter, as in Example 5.

Prepare buffers as in Example 5, with the following pH values:
   a) pH 5.8
   b) pH 6.0
   c) pH 6.2
   d) pH 6.4
   e) pH 6.6
   f) pH 6.8
   g) pH 7.0
   h) pH 7.2

| | |
|---|---|
| In 1.5 ml plastic centrifuge tubes add: | 3 microLiters of stock transporter solution<br>1000 microLiters of one of the 8 buffer solutions<br>15 microLiters of red cell ghost suspension |
| For controls prepare:<br>(no ghosts) | 3 microLiters of stock transporter solution<br>1000 microLiters of pH 6.6 buffer solution<br>15 microLiters of normal saline |
| (no transporter) | 3 microLiters of normal saline<br>1000 microLiters of pH 6.6 buffer solution<br>15 microLiters of red cell ghost suspension |

Cap the tubes, mix well, incubate at 37 degrees C. in waterbath. After the 37 degree incubation, quickly centrifuge in microcentrifuge (10,000 rpm, 10 min).

Carefully (without disturbing the ghost pellet) remove 0.8 ml of each supernatant and add it to 0.2 ml of 1.0 M NaOH, and then measure the absorbance of this initial supernatant at 496 nm. Next, carefully draw off and discard the remaining supernatant from the pellet in each tube, then add to the pellet 0.8 ml of water and 0.2 ml of 1.0 M NaOH to extract transporter component from the ghost pellet, mix well, again centrifuge down the ghosts, and then measure the absorbance of this second supernatant (extract of pellet) at 496 nm. Lastly, plot the absorbance values for both the initial supernatants and the second supernatants (extracts of pellets) as a function of pH. The pH at which the two plots cross is the pH of entry, or pE value, for that transporter peptide.

Example 7

Cell Entry Studies with Cultured Cells

Binding studies with live metabolically active cultured cells are recommended to further confirm the pE values obtained with red cell ghosts. These tests add the important factor of a cytosolic compartment having a pH typically in the range of about 7.2 to 7.5.

Stock solution of transporter composition: To begin, prepare a 2 milliMolar isotonic solution of transporter peptide in its sodium salt form, as follows: weigh out 20 microMoles of fluorescein-tagged transporter component in its free acid form (typically about 70 to 100 milligrams). Add 546 milligrams of mannitol, 9.5 milliLiters of water, and 0.1 milliLiter of 1 Molar aqueous NaOH. Using a pH meter with a microprobe, while stirring slowly add more 1 M aqueous NaOH to effect complete disolution of the transporter composition and raise the pH to about 8.0 (typically requires about an additional 0.1 ml of NaOH solution). Cap and sterilize for 30 minutes at 120 degrees. Alternatively, the transporter solution can be sterilized by passing through a sterile 0.2 micron filter.

Preparation of nine buffered media: Next, prepare 3 portions of Minimum Essential Medium Eagle (MEM) cell culture medium. Each the three portions is buffered using one or the three buffers described in Example 5. Specifically, to one portion add MES buffer to a concentration of 50 milliMole, and then while stirring and monitoring pH, slowly add 1.0 M NaOH to give the desired pH values. When a desired pH is reached, set aside a suitable portion and continue the titration to the next desired pH. For the MES-buffered medium prepare portions at pH 5.8, 6.0, 6.2, and 6.4. Repeat this process with medium buffered with ACES, and take portions at pH 6.6, 6.8, and 7.0. Repeat the process with medium buffered with HEPES, and take portions at pH 7.2 and 7.4. Each portion of these 9 buffered media should then be passed through a 0.2 micron sterile filter into a sterile vial, capped and then stored at 4 degrees C. until use.

Preparation of cultured cells: Seed Hela cells into two 24-well culture plates and allow cells to grow to confluency in 1 ml (each well) of DMEM-F12 media (Catalog # 11330-032, Gibco BRL, Gaithersburg, Md.) containing 5% fetal bovine serum. Wash cells in each well with MEM (without serum), and then wash 9 sets of wells, three wells per set, where each set is washed with one of the nine buffered media prepared above. Next, add to each of three wells in a set 1 ml of that same buffered medium (without serum) to which has been added 10 microLiters of stock transporter solution. Swirl and place in 37 degree C. incubator for 2 hours. After the 2 hour incubation, wash each of the three wells of a set with three 1 ml portions of the same buffered medium (without serum) pre-warmed to 37 degrees C., but lacking the transporter solution.

Observe the washed cells under a fluorescent microscope. Photograph each well of cells first using phase contrast, and then in the fluoresence mode. Lastly, add to each well 0.8 ml of water and 0.2 ml of 1.0 M NaOH to extract transporter component from the cells, swirl for 1 minute, transfer each solution to a 1.5 ml centrifuge tube, centrifuge (10,000 rpm, 10 min) to pellet cell debris, and then use a spectrofluorometer to measure the fluorescence of the supernatant. Note: generally there is too little fluorescence in the samples to get a reliable absorbance reading, and so a fluorescence measurement is typically needed. Lastly, plot the emission values as a function of pH. The pH at which the emission has dropped to half of the maximum value is taken as the pH of entry, or pE value.

It is recommended that this test be repeated, but with buffered media containing 5% fetal calf serum, but only at pH values of 6.4, 6.6, 6.8, 7.0, 7.2 and 7.4 (going below pH 6.4 can cause precipitation of serum proteins). This study in the presence of serum provides information on transporter activity in those areas of tumors where the capillary walls are sufficiently leaky to allow serum proteins to enter the interstitial space of the tumor.

Cell entry studies, as described above, should also be carried out with transporter compositions containing therapeutic moieties to confirm both that the transporter composition can be transported into the cells and that the selected therapeutic moiety of the transporter composition is effective for killing the cells which the transporter composition has entered.

Example 8

Studies in Tumor-Bearing Animals

The easiest in vivo test of transporter activity for diagnostic applications is to prepare technetium-labeled diagnostic transporter compositions, such as shown in FIG. 17. Each transporter composition, formulated as in Example 7 and complexed with technetium, is then injected into a tumor-bearing mouse or larger mammal and then that test subject scanned with a gamma scintillation camera periodically over a period of up to about 24 hours to assess the amount of technetium remaining in the body, as well as the ratio in tumor versus in normal tissue.

Said tests should be carried out both as above, and also with pre-treatment to further reduce the pH within acidic areas of tumors, as described in section V part B.

For assessing in vivo transporter activity for therapeutic applications it may be desirable to obtain more precise information with respect to spatial distribution of the transporter composition within the tumor. For this purpose it is recommended that transporter compositions be prepared with structures as in FIG. 17, but wherein the chelator moiety is replaced with a fluorescein or tetraethylrhodamine moiety. The test animal is injected with a composition of this type and, after a suitable period of time for extracellular material to be cleared from the body, the tumor is excised, frozen, thin slices of that tumor taken in a cryostat, and the slices viewed under a fluorescent microscope. Results from such studies can provide useful information regarding the microscopic distribution of transporter composition within the tumor. This level of precision in assessing spatial distribution of the transporter composition can answer key questions such as the following.

a) Is the transporter composition largely limited to areas fairly close to capillaries, and so apparently failing to reach more acidic areas further from the capillaries? This is a possible limitation when the pE of the transporter is too high.

b) Is the transporter composition only labeling areas of the tumor most distant from the capillaries, while failing to enter into cells in less acidic areas closer to capillaries? This is a possible limitation when the pE of the transporter is too low.

It is envisioned that answers to such questions will be valuable in guiding the development of an optimal transporter composition or combination of transporter compositions for therapeutic applications.

These more detailed fluorescent microscope-based spatial distribution studies should be carried out both as above, and also with pre-treatment to further reduce the pH within acidic areas of tumors, as described in section V part B.

SCOPE OF THE INVENTION

The above presents a description of the best mode contemplated of carrying out the present invention, and of the manner and process of making and using it, in such full, clear, and exact terms as to enable a person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A transporter composition for transporting a moiety into cells in acidic areas of a tumor, wherein said transporter composition comprises
   (a) a transporter peptide which is poly-anionic at pH 7.2 and above, and that converts to a lipophilic form effective to transport into cells at a pH below 7.2 that is present in acidic areas of a tumor, said transporter peptide containing
      (xi) a peptide sequence ranging in length from about 16 to about 50 amino acids,
      (xii) wherein said peptide sequence contains at least three acid pairs, where said acid pairs except for the acid pair closest to the entry end are selected from the group consisting of EE, ELLE, and ELLLE,
      (xiii) each acid of the acid pairs of said peptide sequence except for the acid closest to the entry end is a side chain carboxyl of glutamic acid,
      (xiv) the acid closest to the entry end is selected from the group consisting of a side chain carboxyl of glutamic acid and another carboxyl-containing side chain effective to form an acid pair with a nearby glutamic acid side chain,
      (xv) the number of acid side chains in the core transporter peptide sequence of said peptide sequence is less than 40% of the total side chains in the core transporter peptide sequence,
      (xvi) in said peptide sequence the axial center point of one acid pair relative to the axial center point of the adjacent acid pair along the alpha-helical peptide backbone is rotated by a number of degrees selected from the group consisting of 450, 500, 550, 600, and 650 degrees, except for the rotation between an EE acid pair and an ELLE acid pair which is 700 degrees, and the rotation between an EE acid pair and an ELLLE acid pair which is 750 degrees, (xvii) the average of the axial rotations between acid pairs in said peptide sequence is greater than 500 degrees, wherein 'L' is a lipophilic amino acid selected from the group consisting of leucine, isoleucine, norleucine and methionine, (xviii) at least 90% of the non-acid side chain amino acids of said peptide sequence are lipophilic amino acids (L) selected from the group consisting of leucine, isoleucine, norleucine and methionine, (xix) the entry end of said peptide sequence is predominantly non-ionic at a pH that is present in acidic areas of a tumor, (xx) at least 90% of the amino acids of said peptide sequence are of the same chirality; and, (b) a cargo component which can be pulled across a cell membrane by the transporter peptide, and which contains at least one moiety selected from the group consisting of a diagnostic moiety and a therapeutic moiety.

2. The transporter composition of claim 1 wherein at least 90% of the amino acids of the transporter peptide sequence have D chirality.

3. The transporter composition of claim 1 wherein the cargo component contains at least one diagnostic moiety which is effective for in vivo detection of cells into which the transporter composition has entered.

4. The transporter composition of claim 1 wherein the cargo component includes at least one moiety effective to bind a radioactive element, and which further includes that radioactive element.

5. The transporter composition of claim 4 wherein the radioactive element is technetium 99.

6. The transporter composition of claim 1 wherein the cargo component contains at least one therapeutic moiety which is effective to kill cells into which the transporter composition has entered.

7. The transporter composition of claim 6 wherein the cargo component includes a radioisotope.

8. The transporter composition of claim 6 wherein the cargo component includes a toxin.

9. A composition for transporting a moiety into cells, wherein said composition comprises (a) a peptide which includes an amino acid sequence motif selected from the group consisting of ELLLELELLELLLE and ELLELELLLELELLEL wherein 'L' is a lipophilic amino acid selected from the group consisting of leucine, isoleucine, norleucine and methionine; and, (b) a moiety which can be pulled across a cell membrane by said peptide.

10. The composition of claim 9, which has the structure Moiety-LELLLELELLELELLLELELLELELLLE(L)n-(NH—CH2—CH(CH3)$_2$), wherein n is selected from the group consisting of one, two, and three.

11. A method for transporting a moiety into cells in acidic areas of a tumor in an animal, said method comprising (a) providing an improved transporter composition including a transporter peptide which is poly-anionic at pH 7.2 and above, and that converts to a lipophilic form effective to transport into cells at a pH below 7.2 that is present in acidic areas of a tumor, said transporter peptide containing (i) a peptide sequence ranging in length from about 16 to about 50 amino acids, (ii) wherein said peptide sequence contains at least 3 acid pairs, where said acid pairs except for the acid pair closest to the entry end are selected from the group consisting of EE, ELLE, and ELLLE, wherein 'L' is a lipophilic amino acid selected from the group consisting of leucine, isoleucine, norleucine and methionine, (iii) each acid of the acid pairs of said peptide sequence except for the acid closest to the entry end is a side chain carboxyl of glutamic acid, (iv) the acid closest to the entry end is selected from the group consisting of a side chain carboxyl of glutamic acid and another carboxyl-containing side chain effective to form an acid pair with a nearby glutamic acid side chain, (v) the number of acid side chains in the core transporter peptide sequence of said peptide sequence is less than 40% of the total side chains in the core transporter peptide sequence, (vi) in said peptide sequence the axial center point of one acid pair relative to the axial center point of the adjacent acid pair along the alpha-helical peptide backbone is rotated by a number of degrees selected from the group consisting of 450, 500, 550, 600, and 650 degrees, except for the rotation between an EE acid pair and an ELLE acid pair which is 700 degrees, and the rotation between an EE acid pair and an ELLLE acid pair which is 750 degrees, (vii) the average of the axial rotations between acid pairs in said peptide sequence is greater than 500 degrees, (viii) at least 90% of the non-acid side chain amino acids of said peptide sequence are lipophilic amino acids (L) selected from the group consisting of leucine, isoleucine, norleucine and methionine, (ix) the entry end of said peptide sequence is predominantly non-ionic at a pH that is present in acidic areas of a tumor, (x) at least 90% of the amino acids of said peptide sequence are of the same chirality, and a cargo component which can be pulled across a cell membrane by the transporter peptide, and which contains at least one moiety selected from the group consisting of a diagnostic moiety and a therapeutic moiety, and (b) introducing said transporter composition into the animal.

12. The method of claim 11 wherein the animal is a human.

13. A method for detecting in a patient tumors which have acidic areas, said method comprising (a) providing at least one improved transporter composition of claim 1 wherein the cargo component contains at least one diagnostic moiety, (b) introducing at least one said composition into the patient, (c) waiting for a period of time of about one to about twenty-four hours to allow clearance of said composition which has not entered cells, and (d) scanning the patient with equipment effective to detect the position and amount of said composition remaining in the patient.

14. The method of claim 13 which also includes first treating the patient with a substance effective to temporarily further reduce the pH in acidic areas of tumors.

15. The method of claim 14 where said substance includes glucose.

16. A method for treating tumors in a patient, said method comprising
  (a) providing at least one improved transporter composition of claim 1 wherein the cargo component contains at least one therapeutic moiety, and
  (b) introducing at least one said composition into the patient.

17. The method of claim 16 wherein the patient also receives conventional cancer therapy selected from the group consisting of chemotherapy and radiation that is effective to kill fast-dividing cells of tumors.

18. The method of claim 16 which includes first treating the patient with a substance effective to temporarily further reduce the pH in acidic areas of tumors.

19. The method of claim 18 where said substance includes glucose.

20. The method of claim 18 wherein the patient also receives conventional cancer therapy selected from the group consisting of chemotherapy and radiation that is effective to kill fast-dividing cells of tumors.

21. A method for transporting a moiety into cells in acidic areas of a tumor in a patient, said method comprising
  (a) providing a transporter composition including
    a transporter peptide which is poly-anionic at pH 7.2 and above, and that converts to a lipophilic form effective to transport into cells at a pH below 7.2 that is attainable in acidic areas of a tumor, said transporter peptide containing
      (ii) a peptide sequence ranging in length from about 16 to about 50 amino acids,
      (ii) wherein said peptide sequence contains at least three acid pairs, wherein said acid pairs, except for the acid pair closest to the entry end, are selected from the group consisting of EE, ELLE, and ELLLE, wherein 'L' is a lipophilic amino acid selected from the group consisting of leucine, isoleucine, norleucine and methionine,
      (iii) each acid of the acid pairs of said peptide sequence except for the acid closest to the entry end is a side chain carboxyl of glutamic acid,
      (iv) the acid closest to the entry end is selected from the group consisting of a side chain carboxyl of glutamic acid and another carboxyl-containing side chain effective to form an acid pair with a nearby glutamic acid side chain,
      (v) the number of acid side chains in the core transporter peptide sequence of said peptide sequence is less than 45% of the total side chains in the core transporter peptide sequence,
      (vi) in said peptide sequence the axial center point of one acid pair relative to the axial center point of the adjacent acid pair along the alpha-helical peptide backbone is rotated by a number of degrees selected from the group consisting of 450, 500, 550, 600, and 650 degrees, except for the rotation between an EE acid pair and an ELLE acid pair which is 700 degrees, and the rotation between an EE acid pair and an ELLLE acid pair which is 750 degrees,
      (vii) the average of the axial rotations between acid pairs in said peptide sequence is at least 450 degrees,
      (viii) at least 90% of the non-acid side chain amino acids of said peptide sequence are lipophilic amino acids (L) selected from the group consisting of leucine, isoleucine, norleucine and methionine,
      (ix) the entry end of said peptide sequence is predominantly non-ionic at a pH that is present in acidic areas of a tumor,
      (x) at least 90% of the amino acids of said peptide sequence are of the same chirality, and
    a cargo component which can be pulled across a cell membrane by the transporter peptide, and which contains at least one moiety selected from the group consisting of a diagnostic moiety and a therapeutic moiety,
  (b) treating the patient with a substance effective to temporarily further reduce the pH in acidic areas of tumors, and
  (c) introducing said transporter composition into the patient.

22. The method of claim 21 wherein said substance to temporarily further reduce the pH in acidic areas of tumors includes glucose.

23. The method of claim 21 wherein the patient also receives conventional cancer therapy selected from the group consisting of chemotherapy and radiation that is effective to kill fast-dividing cells of tumors.

24. A precursor form of a transporter composition for transporting a moiety into cells in acidic areas of a tumor, wherein said precursor form of a transporter composition comprises
  (a) a transporter peptide which is poly-anionic at pH 7.2 and above, and that converts to a lipophilic form effective to transport into cells at a pH below 7.2 that is present in acidic areas of a tumor, said transporter peptide containing
    (i) a peptide sequence ranging in length from about 16 to about 50 amino acids,
    (ii) wherein said peptide sequence contains at least three acid pairs, where said acid pairs except for the acid pair closest to the entry end are selected from the group consisting of EE, ELLE, and ELLLE, wherein 'L' is a lipophilic amino acid selected from the group consisting of leucine, isoleucine, norleucine and methionine,
    (iii) each acid of the acid pairs of said peptide sequence except for the acid closest to the entry end is a side chain carboxyl of glutamic acid,
    (iv) the acid closest to the entry end is selected from the group consisting of a side chain carboxyl of glutamic acid and another carboxyl-containing side chain effective to form an acid pair with a nearby glutamic acid side chain,
    (v) the number of acid side chains in the core transporter peptide sequence of said peptide sequence is less than 40% of the total side chains in the core transporter peptide sequence,
    (vi) in said peptide sequence the axial center point of one acid pair relative to the axial center point of the adjacent acid pair along the alpha-helical peptide backbone is rotated by a number of degrees selected from the group consisting of 450, 500, 550, 600, and 650 degrees, except for the rotation between an EE acid pair and an ELLE acid pair which is 700 degrees, and the rotation between an EE acid pair and an ELLLE acid pair which is 750 degrees,
    (vii) the average of the axial rotations between acid pairs in said peptide sequence is greater than 500 degrees,
    (viii) at least 90% of the non-acid side chain amino acids of said peptide sequence are lipophilic amino acids (L) selected from the group consisting of leucine, isoleucine, norleucine and methionine, (ix) the entry end of said peptide sequence is predominantly non-ionic at a pH that is present in acidic areas of a tumor,
(x) at least 90% of the amino acids of said peptide sequence are of the same chirality; and,
(b) a precursor to a cargo component, where said precursor is reactive toward a substance such that when said precursor and said substance are contacted they form a cargo component which can be pulled across a cell membrane by the transporter peptide, and which contains at least one moiety selected from the group consisting of a diagnostic moiety and a therapeutic moiety.

25. The composition of claim 24 wherein said precursor to a cargo component contains a chelator moiety effective to bind a radioactive substance.

* * * * *